(12) United States Patent
Monahan et al.

(10) Patent No.: US 7,601,367 B2
(45) Date of Patent: Oct. 13, 2009

(54) COMPOSITIONS AND PROCESSES USING SIRNA, AMPHIPATHIC COMPOUNDS AND POLYCATIONS

(75) Inventors: Sean D. Monahan, Madison, WI (US); David L. Lewis, Madison, WI (US); Hans Herweijer, Madison, WI (US); Jon A. Wolff, Madison, WI (US); James E. Hagstrom, Middleton, WI (US); Aaron G. Loomis, Prairie du Sac, WI (US); Vladimir Trubetskoy, Middleton, WI (US); Lori Higgs, Madison, WI (US)

(73) Assignee: Mirus Bio LLC, Madison, WI (US)

( * ) Notice: Subject to any disclaimer, the term of this patent is extended or adjusted under 35 U.S.C. 154(b) by 140 days.

(21) Appl. No.: 10/845,968

(22) Filed: May 14, 2004

(65) Prior Publication Data

US 2005/0143332 A1 Jun. 30, 2005

Related U.S. Application Data

(63) Continuation-in-part of application No. 10/345,021, filed on Jan. 15, 2003, now abandoned, and a continuation-in-part of application No. 10/186,757, filed on Jul. 1, 2002, now abandoned, and a continuation-in-part of application No. 10/157,674, filed on May 28, 2002, now Pat. No. 7,101,995.

(51) Int. Cl.
*A61K 9/127* (2006.01)
*C07H 21/04* (2006.01)
*C12N 15/88* (2006.01)

(52) U.S. Cl. .................. 424/450; 536/24.5; 435/458

(58) Field of Classification Search ............... None
See application file for complete search history.

(56) References Cited

U.S. PATENT DOCUMENTS

| 5,744,335 | A | 4/1998 | Wolff et al. |
|---|---|---|---|
| 6,180,784 | B1 | 1/2001 | Wolff et al. |
| 6,291,423 | B1 * | 9/2001 | Bischoff et al. ............... 514/2 |
| 7,101,995 | B2 * | 9/2006 | Lewis et al. .................. 536/55 |
| 2003/0125281 | A1 | 7/2003 | Lewis et al. |
| 2003/0143204 | A1 | 7/2003 | Lewis et al. |
| 2004/0019008 | A1 * | 1/2004 | Lewis et al. .................. 514/44 |

OTHER PUBLICATIONS

Oku et al. (Nov. 2001) Adv. Drug Deliv. Rev. 52:209-218.*
Bernstein et al., "Role for a bidentate ribonuclease in the initiation step of RNA interference," Nature; Jan. 2001, vol. 409, pp. 363-366.
Caplen et al., "dsRNA-mediated gene silencing in cultured drosophila cells: a tissue culture model for the analysis of RNA interference," Gene; 2000, vol. 252, pp. 95-105.
Caplen et al., "Specific inhibition of gene expression by small double-stranded RNAs in invertebrate and vertebrate systems," PNAS; 2001, vol. 98, No. 17.
Catalanotto et al., "Gene silencing in worms and fungi," Nature; Mar. 2000, vol. 404, p. 245.
Clemens et al., "The double-stranded RNA-dependent protein kinase PKR: structure and function," Journal of Interferon and Cytokine Research; 1997, vol. 17, pp. 503-524.
Elbashir et al., "Duplexes of 21-nucleotide RNAs mediate RNA interference in cultured mammalian cells," Nature; May 2001, vol. 41, pp. 494-498.
Elbashir et al., "RNA interference is mediated by 21- and 22-nucleotide RNAs," Genes and Development; 2001, vol. 15, pp. 188-200.
Fagard et al., "AG01, QDE-2, and RDE-1 are related proteins required for post-transcriptional gene silencing in plants, quelling in fungi, and RNA interference in animals," PNAS; Oct. 2000, vol. 97, No. 21, pp. 11650-11654.
Gao et al., "A novel cationic liposome reagent for efficient transfection of mammalian cells," Biochemical and Biophysical Research Communications; Aug. 1991, vol. 179, No. 1, pp. 280-285.
Hamilton et al., "A species of small antisense RNA in post-transcriptional gene silencing in plants," Science; Oct. 1999, vol. 286, pp. 950-952.
Hammond et al., "An RNA-directed nuclease mediates post-transcriptional gene silencing in drosophila cells," Nature; Mar. 2000, vol. 404, pp. 293-296.
Hammond et al., "Post-transcriptional gene silencing by double-stranded RNA," Nature; Feb. 2001, vol. 2, pp. 110-119.
Ketting et al., "mut-7 of C. elegans, required for transposon silencing and RNA interference, is a homolog of Werner syndrome helicase and RnaseD," Cell; Oct. 1999, vol. 99, pp. 133-141.
Leventis et al., "Interactions of mammalian cells with lipid dispersions containing novel metabolizable cationic amphiphiles," Biochimica et Biophysica Acta.; 1990, vol. 1023, pp. 124-132.
Manche et al., "Interactions between double-stranded RNA regulators and the protein kinase DAI," Molecular and Cellular Biology; Nov. 1992, vol. 12, No. 11, pp. 5238-5248.
Minks et al., "Structural requirements of Double-Stranded RNA for the activation of 2', 5'-oligo(A) polymerase and protein kinase of interferon-treated HeLa Cells," The Journal of Biological Chemistry; Oct. 1979, vol. 254, No. 30, pp. 10180-10183.
Parrish et al., "Functional anatomy of a dsRNA trigger: differential requirement for the two trigger strands in RNA interference," Molecular Cell; Nov. 2000, vol. 6, pp. 1077-1087.
Player et al., "The 2-5 system: Modulation of Viral and cellular processes through acceleration of RNA degradation," Pharmacol. Ther.; 1998, vol. 78, No. 2, pp. 55-113.
Reidhaar-Olson et al., "The impact of genomics tools on target discovery," Current Drug Discovery; Apr. 2001.

(Continued)

*Primary Examiner*—Richard Schnizer
(74) *Attorney, Agent, or Firm*—Mark K Johnson

(57) ABSTRACT

Described is a deliverable composition with low toxicity comprising an amphipathic compound, a polycation, and a siRNA. The composition may be used in the process of delivering a siRNA to an animal cell or more particularly, a mammal cell.

6 Claims, 11 Drawing Sheets

OTHER PUBLICATIONS

Sharp "RNAi and double-strand RNA," Genes and Development; 1999, vol. 13, pp. 139-141.

Sharp et al., "RNA-Interference-2001," Genes and Development; 2001, vol. 15, pp. 485-490.

Stark et al., "How cells respond to interferons," Annu. Rev. Biochem.; 1998, vol. 67, pp. 227-264.

Summerton et al., "Morpholino and phosphorothioate antisense oligomers compared in cell-free and in-cell systems," Antisense and Nucleic Acid Drug Development; 1997, vol. 7, pp. 63-70.

Svoboda et al., "Selective reduction of dormant maternal mRNAs in mouse oocytes by RNA interference," Development; 2000, vol. 127, pp. 4147-4156.

Tabara et al., "The rde-1 gene, RNA interference, and transposon silencing in C. elegans," Cell; Oct. 1999, vol. 99, pp. 123-132.

Tuschl et al., "Targeted mRNA degradation by double-stranded RNA in vitro," Genes and Development; 1999; vol. 13, pp. 3191-3197.

Wianny et al., "Specific interference with gene function by double-stranded RNA in early mouse development," Nature Cell Biology; Feb. 2000, vol. 2, pp. 70-75.

Yang et al., "Evidence that processed small dsRNAs may mediate sequence-specific mRNA degradation during in drosophilia embryos," Current Biology; 2000, vol. 10, pp. 1191-1200.

Zamore et al., "RNAi: Double-stranded RNA directs the ATP-dependent cleavage of mRNA at 21 to 23 nucleotide intervals," Cell; Mar. 2000, vol. 101, pp. 25-33.

Goula D et al. "Size, diffusibility and transfection performance of linear PEI/DNA complexes in the mouse central nervous system." Gene Ther 1998 vol. 5 No. 5 pp. 712-717.

Morcos PA "Achieving efficient delivery of morpholino oligos in cultured cells." Genesis 2001 vol. 30 p. 94-102.

\* cited by examiner

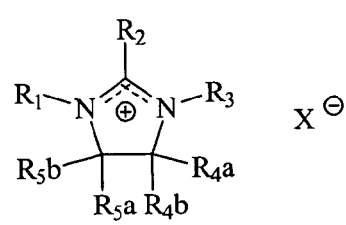
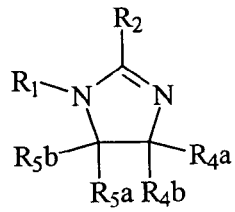
FIG. 2
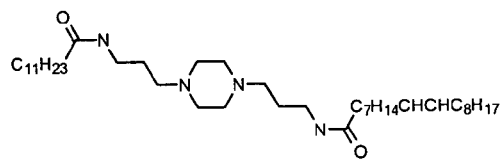
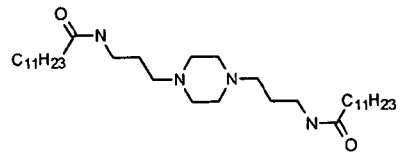
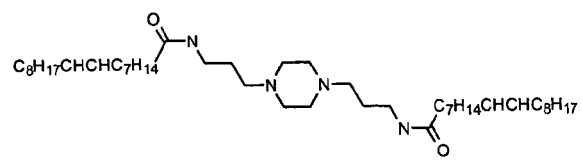
FIG. 3

A.
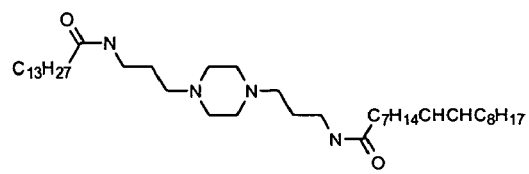
B.
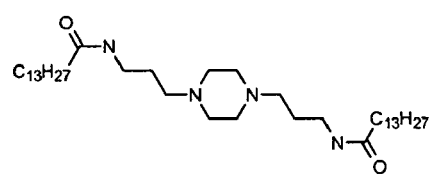
C.
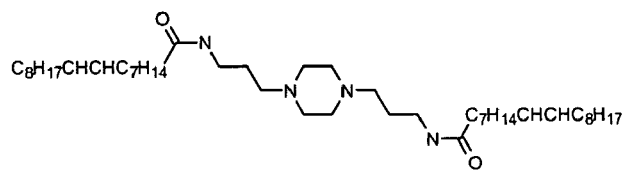
D.
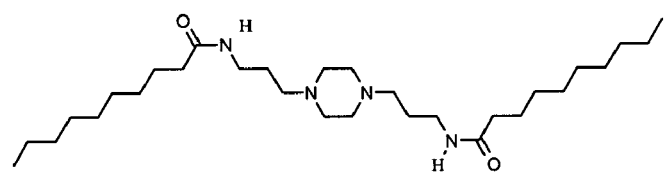
E.
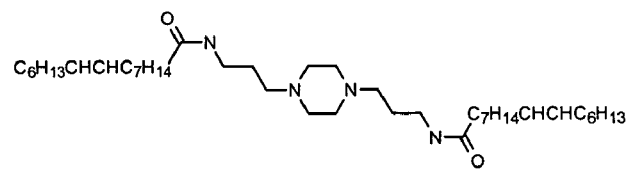
FIG. 4

A.
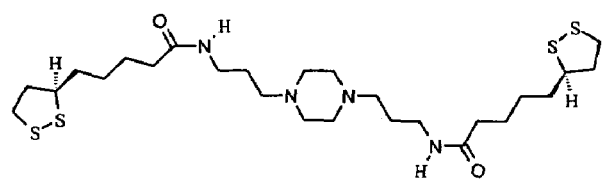
B.
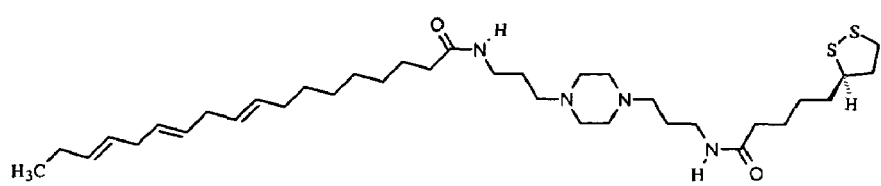
C.
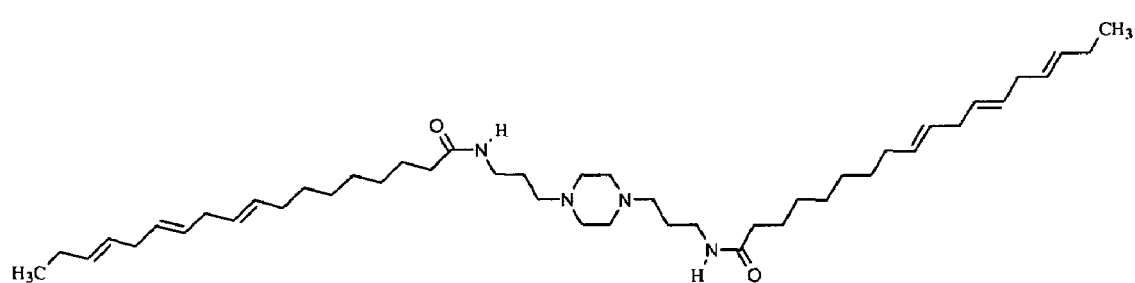
FIG. 5

A.
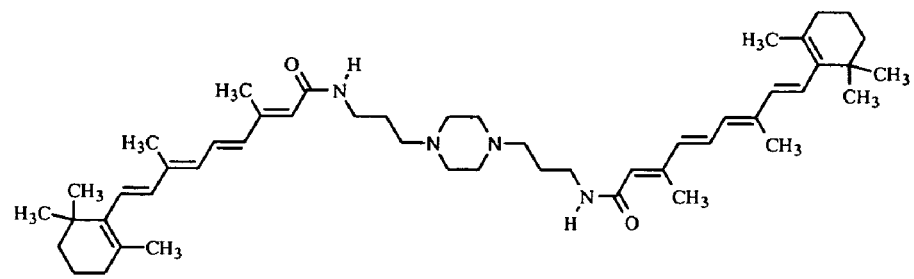
B.
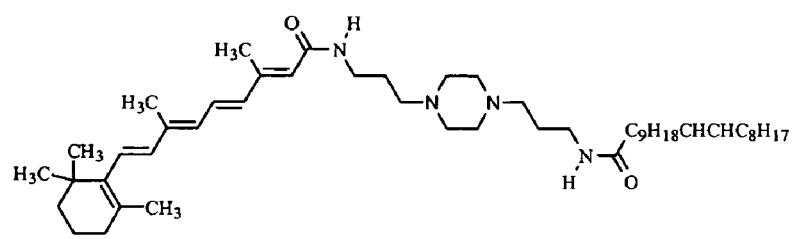
C.
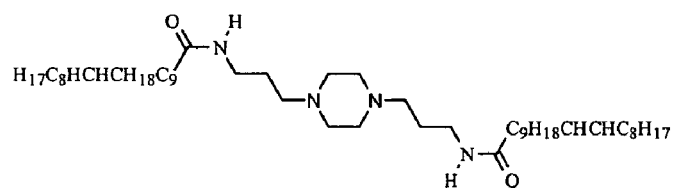
FIG. 6

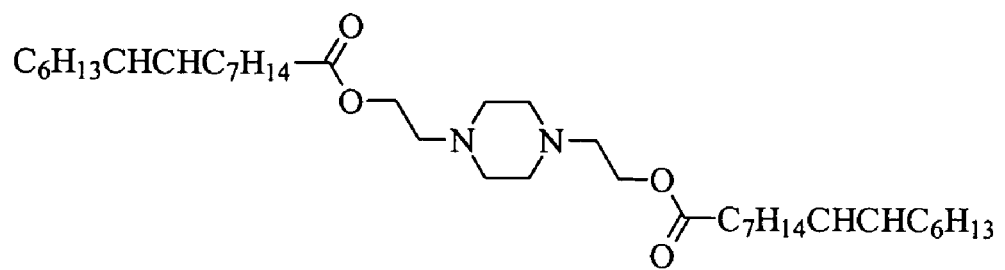
MC 810
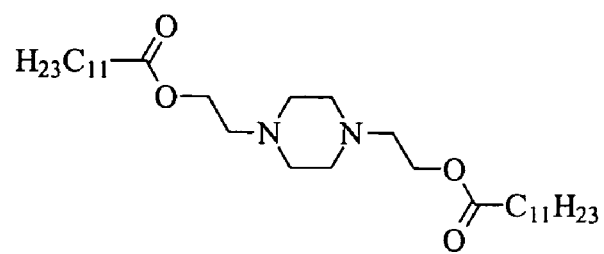
MC 1069
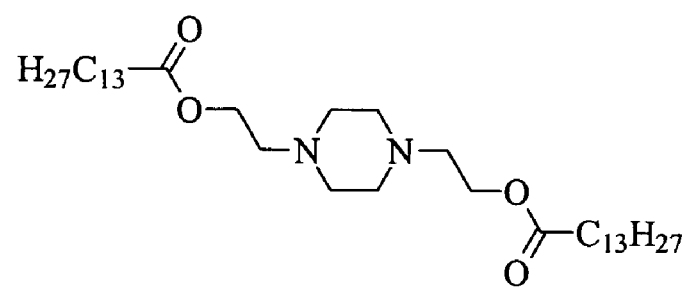
MC 1070
FIG. 7

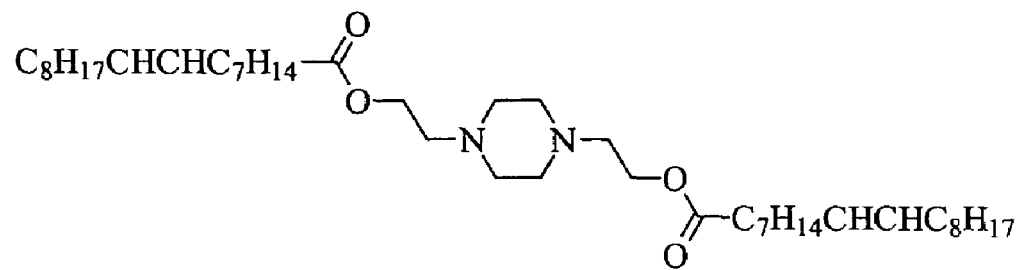
MC1083
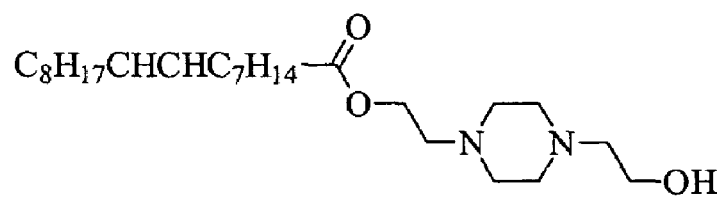
MCMC1086
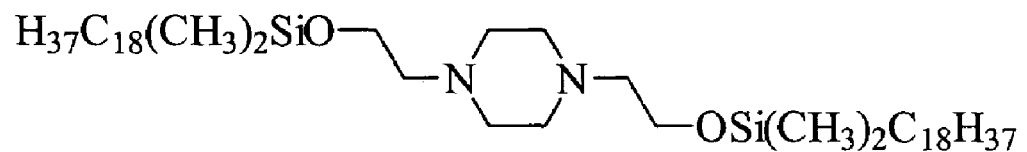
MC1084
FIG. 8

COMPOSITIONS AND PROCESSES USING SIRNA, AMPHIPATHIC COMPOUNDS AND POLYCATIONS

CROSS-REFERENCE TO RELATED APPLICATIONS

This application is a Continuation-In-Part of U.S. application Ser. No. 10/186,757, filed Jul. 1, 2002, abandoned, a continuation-in-part of U.S. application Ser. No. 10/157,674, filed May 28, 2002, now U.S. Pat. No. 7,101,995, and a continuation-in-part of U.S. application Ser. No. 10/345,021, filed Jan. 15, 2003, abandoned.

REFERENCE TO SEQUENCE LISTING

The specification includes a sequence listing for the sequences found in the specification. A sequence listing paper copy has been submitted along with a computer readable form which contains the identical information as the paper copy.

FIELD OF THE INVENTION

The field of the present invention is a composition comprising siRNA, amphipathic compounds and polycations and the use of such compositions for delivering the siRNA to an animal cell.

BACKGROUND

RNA interference (RNAi) is a phenomenon wherein double-stranded RNA, when present in a cell, inhibits expression of a gene that has an identical or nearly identical sequence. Inhibition is caused by degradation of the messenger RNA (mRNA) transcribed from the target gene [Sharp 2001]. The double-stranded RNA responsible for inducing RNAi is termed interfering RNA. The mechanism and cellular machinery through which dsRNA mediates RNAi has been investigated using both genetic and biochemical approaches. Biochemical analyses suggest that dsRNA introduced into the cytoplasm of a cell is first processed into RNA fragments 21-25 nucleotides long [Hammond et al. 2000; Hamilton and Baulcombe 1999; Zamore et al. 2000; Yang et al. 2000; Parrish et al. 2000]. It has been shown in in vitro studies that these dsRNAs, termed small interfering RNAs (siRNA) are generated at least in part by the RNAse III-like enzyme Dicer [Hammond et al. 2000]. These siRNAs likely act as guides for mRNA cleavage, as the target mRNA is cleaved at a position in the center of the region covered by a particular siRNA [Sharp 2001]. Biochemical evidence suggests that the siRNA is part of a multicomponent nuclease complex termed the RNA-induced silencing complex (RISC) [Hammond et al. 2000]. One of the proteins of this complex, Argonaute2, has been identified as a product of the argonaute gene family [Sharp 2001]. This gene family, which also contains the *C. elegans* homolog rde-1 and related genes, the *N. crassa* homolog qde-2, and the *Arabidopsis* homolog arg-1, has been shown to be required for RNAi through genetic studies [Sharp 2001; Hammond et al. 2000; Hamilton and Baulcombe 1999]. Genetic screens in *C. elegans* have also identified the mut-7 gene as essential for RNAi. This gene bears resemblance to RNAse D, suggesting that its gene product acts in the mRNA degradation step of the reaction [Sharp 2001].

Although the use of easily manipulated model systems such as *C. elegans* and *D. melanogaster* in gene function studies can yield clues concerning possible new drug targets in mammals, a more direct approach would be to study gene function in mammalian model systems. It has previously been demonstrated that dsRNA can be used to induce RNAi and inhibit target gene expression in mouse oocytes and early embryos [Sharp 2001; Hammond et al. 2000]. However, data obtained in a number of other studies have indicated that the use of dsRNA to induce RNAi in cultured mammalian cells or post-embryonic tissue may not be effective as a sequence-specific method of gene silencing [Sharp 2001; Hammond et al. 2000]. This discrepancy may be due in large part to the well-documented dsRNA-mediated induction of interferon synthesis, a response pathway not present in oocytes and early embryos. Activation of dsRNA dependent enzymes leads to non-sequence specific effects on cellular physiology and gene expression [Sharp 2001; Hammond et al. 2000; Hamilton and Baulcombe 1999; Zamore et al. 2000]. A major component of the interferon response is the interferon-induced dsRNA-dependent protein kinase, protein kinase R (PKR), which phosphorylates and inactivates the elongation factor eIF2a. In addition, interferons induce the synthesis of dsRNA dependent 2-5(A) synthetases, which synthesize 2'-5' polyadenylic acid leading to the activation of the non-sequence specific RNAse L [Sharp 2001].

The PKR pathway however, is not activated by dsRNA of less than 30 base pairs in length and full activation requires dsRNAs 80 base pairs in length [Manche et al. 1992; Minks et al. 1979]. This fact suggested that if siRNAs are used to initiate RNAi instead of longer dsRNAs, it would be possible to circumvent at least part of the interferon response. Data obtained from studies in which siRNA 21-25 base pairs in length was delivered to mammalian cells in culture indicated that sequence-specific inhibition through RNAi is indeed effective [Sharp 2001; Hammond et al. 2000]. In these studies, gene-specific inhibition was observed in a variety of both immortalized and primary cell lines. The degree of inhibition varied between 80-96% using siRNA targeted against a reporter gene expressed from transiently transfected plasmids containing strong enhancers. Expression of a control reporter gene of unrelated sequence was unaffected by the siRNA, and no inhibition was observed using siRNAs against unrelated sequences. Expression of endogenous genes could also be inhibited to levels below detection by siRNA. These data demonstrate the specificity and effectiveness of siRNA-mediated RNAi in cultured mammalian cell lines and suggest that the interferon response is not activated by siRNAs of this length. These results suggest that RNAi can indeed be used to effectively inhibit gene expression in mammalian cells.

The ability to specifically inhibit expression of a target gene by RNAi has obvious benefits. For example, many diseases arise from the abnormal expression of a particular gene or group of genes. RNAi could be used to inhibit the expression of the deleterious gene and therefore alleviate symptoms of a disease or even provide a cure. For example, genes contributing to a cancerous state or to viral replication could be inhibited. In addition, mutant genes causing dominant genetic diseases such as myotonic dystrophy could be inhibited. Inflammatory diseases such as arthritis could also be treated by inhibiting such genes as cyclooxygenase or cytokines. Examples of targeted organs would include the liver, pancreas, spleen, skin, brain, prostrate, heart etc. In addition, RNAi could be used to generate animals that mimic true genetic "knockout" animals to study gene function.

Drug discovery could also be facilitated by siRNA technology. The siRNA approach for target validation will provide a quicker and less expensive approach to screen potential drug targets. Information for drug targeting will be gained not only by inhibiting a potential drug target but also by determining whether an inhibited protein, and therefore the pathway, has significant phenotypic effects. For example, inhibition of LDL receptor expression should raise plasma LDL levels and, therefore, suggest that up-regulation of the receptor would be of therapeutic benefit. Expression arrays can be used to determine the responsive effect of inhibition on the expression of genes other than the targeted gene or pathway [Sharp 2001]. It will place the gene product within functional pathways and networks (interacting pathways).

The efficient delivery of biologically active compounds to the intracellular space of cells has been accomplished by the use of a wide variety of vesicles. One particular type of vesicle, liposomes, is one of the most developed types of vesicles for drug delivery. Liposomes, which have been under development since the 1970's, are microscopic vesicles that comprise amphipathic molecules which contain both hydrophobic and hydrophilic regions. Liposomes can be formed from one type of amphipathic molecule or several different amphipathic molecules. Several methods have been developed to complex biologically active compounds with liposomes. In particular, polynucleotides complexed with liposomes have been delivered to mammalian cells. After the description of DOTMA (N-[1-(2,3-dioleyloxy)propyl]-N,N, N-trimethylammonium chloride), a number of cationic lipids have been synthesized for this purpose. Essentially all the cationic lipids are amphipathic compounds that contain a hydrophobic domain, a spacer, and positively-charged amine(s). The cationic lipids are sometimes mixed with a fusogenic lipid such as DOPE (dioleoyl phosphatidyl ethanolamine) to form liposomes. The cationic liposomes are then mixed with plasmid DNA and the binary complex of the DNA and liposomes are applied to cells in a tissue culture dish or injected in vivo. The ease of mixing the plasmid DNA with the cationic liposome formulation, the ability of the cationic lipids to complex with DNA and the relative high levels of transfection efficiency has led to increasing use of these formulations. However, these cationic lipid formulations have a common deficiency in that they are typically toxic to the cells in culture and in vivo [Catalanotto et al. 2000]. More recently lipids have been used in association with other DNA-binding compounds to facilitate transfection of cells. The present invention provides new amphipathic compounds, and methods of preparation thereof, to be used to prepare novel complexes of biologically active polyions for delivery to animal cells in vitro and in vivo. The complexes facilitate high efficiency transfer of the polyion from outside the cell to the inside a cell with low toxicity.

The present invention describes transfection reagents and methods to deliver siRNA to animal cells in vitro and in vivo with high efficiency and low toxicity. We demonstrate that our method effectively delivers siRNA to animal cells for the purpose of RNA interference.

SUMMARY

The present invention provides siRNA transfer into animal cells using a ternary complex comprising siRNA, an amphipathic compound, and a polycation. Novel amphipathic compounds and methods of preparation thereof, are described. In a preferred embodiment, compositions comprising siRNAs, amphipathic compounds and polycations, and processes using such compositions to deliver a siRNA to an animal cell in vivo or in vitro for the purposes of inhibiting expression of a gene in the cell are described.

The present invention provides siRNA transfer into animal cells using a quaternary complex comprising siRNA, a first amphipathic compound, a second amphipathic compound and a polycation. Novel amphipathic compounds and methods of preparation thereof, are described. In a preferred embodiment, compositions comprising siRNAs, amphipathic compounds and polycations, and processes using such compositions to deliver a siRNA to an animal cell in vivo or in vitro for the purposes of inhibiting expression of a gene in the cell are described.

In a preferred embodiment, compositions and compounds are described that facilitate delivery of siRNA to an animal cell in vitro and in vivo. The siRNA comprises a double-stranded structure having a nucleotide sequence substantially identical to an expressed target gene within the cell. Further, the use of a polycation and one or more novel amphipathic compounds together significantly increased siRNA transfer efficiency. The siRNA then inhibits expression of a selected target gene.

In a preferred embodiment, the polycation is a polymer such as poly-L-lysine, polyvinylamine, polyethylenimine (PEI), polysilazane, polydihydroimidazolenium, polyallylamine and the like. A preferred cationic polymer is polyvinylamine.

In a preferred embodiment the polycation is a DNA-binding protein. A preferred DNA-binding protein is a histone such as H1, H2A, or H2B. The histone can be from a natural source such as calf thymus or can be recombinant protein produced in bacteria. DNA-binding proteins such as histone have several advantages over polycationic compounds such as polylysine. Human H1 histone protein is not immunogenic and does not induce anaphylaxis. Polylysine induces anaphylactic shock and is very immunogenic. In a preferred embodiment, the DNA-binding protein is linked to a nuclear localization signal such as a recombinant histone produced in bacteria containing both the SV40 large T antigen nuclear localization signal and the C-terminal domain of human histone H1, (NLS-H1).

In a preferred embodiment, polyvinylamine or a similar polymer is used as the polycation and one or more compounds of the structures shown in FIG. 1 are used as amphipathic compound(s). In another preferred embodiment, histone H1 protein is used as the polycation and a compound of structure #1 is used as the amphipathic compound. The siRNA can be used to study the target gene's effect on the cell or to affect a therapeutic change in the cell.

In a preferred embodiment, the cell can be an animal cell that is maintained in tissue culture such as cell lines that are immortalized or transformed. These include a number of cell lines that can be obtained from American Type Culture Collection (Bethesda) such as, but not limited to: 3T3 (mouse fibroblast) cells, Rat1 (rat fibroblast) cells, CHO (Chinese hamster ovary) cells, CV-1 (monkey kidney) cells, COS (monkey kidney) cells, 293 (human embryonic kidney) cells, HeLa (human cervical carcinoma) cells, HepG2 (human hepatocytes) cells, Sf9 (insect ovarian epithelial) cells and the like.

In another preferred embodiment, the cell can be a primary or secondary cell which means that the cell has been maintained in culture for a relatively short time after being obtained from an animal. These include, but are not limited to, primary liver cells and primary muscle cells and the like. The cells within the tissue are separated by mincing and digestion with enzymes such as trypsin or collagenases which destroy the extracellular matrix. Tissues consist of several different cell types and purification methods such as gradient centrifugation or antibody sorting can be used to obtain purified amounts of the preferred cell type. For example, primary myoblasts are separated from contaminating fibroblasts using Percoll (Sigma) gradient centrifugation.

In another preferred embodiment, the cell can be an animal cell that is within the tissue in situ or in vivo meaning that the cell has not been removed from the tissue or the animal.

In a preferred embodiment a process is describes for delivering an siRNA into an animal cell for the purposes of inhibiting expression of a gene (called RNA interference) comprising forming a complex comprising one or more amphipathic compounds, an effective amount of a polycation and an siRNA in solution, and associating the cell with the complex. A preferred amphipathic compound is a compound of structure shown in FIG. 1. A preferred polycation is ethoxylated PEI. Another preferred polycation is polyvinylamine.

A variety of amphipathic compounds can be used in conjunction with a polycation to mediate the transfer of the siRNA into the cell. In a preferred embodiment the amphipathic compound is cationic. The cationic amphipathic compound can be a non-natural polyamine wherein one or more of the amines is bound to at least one hydrophobic moiety wherein the hydrophobic moiety comprises a C6-C24 alkane, C6-C24 alkene, mono-, di-, or tri-substituted alkyl silane, sterol, steroid, lipid, fatty acid or hydrophobic hormone. The amphipathic compounds may or may not form liposomes. In a preferred embodiment, several novel amphipathic cationic compounds are described. These compounds have the general structure comprising the structure shown in FIG. 1, wherein $R_1$ and $R_2$ come from the group consisting of C6-C24 alkane, C6-C24 alkene, mono-, di-, or tri-substituted alkyl silane, sterol, steroid, lipid, fatty acid or hydrophobic hormone or other similar hydrophobic group. $R_1$ and $R_2$ may be identical or they may be different. Alkyl silane substitutions of the bis-aminopropylpiperazine (shown on the left in FIG. 1) are generally hydrolytically labile.

In contrast to the use of previously described cationic liposomes for gene transfer, most of the novel amphipathic cationic compounds described above do not efficiently mediate the transfer of genes into cells when used alone. However, the use of polycations with these novel amphipathic cationic compounds enables the efficient gene transfer into a variety of animal cells with minimal cellular toxicity. The combination of polycation and amphipathic compounds enhances the efficiency of siRNA delivery.

In a preferred embodiment, the present invention provides a process for delivering a siRNA to an animal cell comprising; preparing a ternary or quaternary complex comprising mixing a one or two compounds of structure shown in FIG. 1 with a siRNA and a polycation in a solution, associating the complex with an animal cell, and delivering the siRNA to the interior of the cell. The siRNA then inhibits expression of a gene in the cell. The amphipathic compound may be mixed with the polycation prior to addition of the siRNA, at the same time as the siRNA, or after the siRNA.

In a preferred embodiment, we describe a complex for inhibiting nucleic acid expression in a cell. The complex comprises mixing a siRNA and a compound or compounds to form the complex wherein the zeta potential of the complex is less negative than the zeta potential of the siRNA alone. Then inserting the complex into a mammalian blood vessel, in vivo, and delivering the complex to the cell wherein the expression of a selected gene is inhibited.

In a preferred embodiment, the polycation, the siRNA, or the amphipathic compound may be modified by attachment of a functional group. The functional group can be, but is not limited to, a targeting signal or a label or other group that facilitates delivery of the siRNA. The group may be attached to one or more of the components prior to complex formation. Alternatively, the group(s) may be attached to the complex after formation of the complex.

In a preferred embodiment, the present invention describes a process of delivering a siRNA to an animal cell comprising associating the cell with a complex comprising an one or more different amphipathic compounds, an effective amount of a polycation and a selected siRNA in solution. The term deliver means that the siRNA becomes associated with the cell thereby altering the endogenous properties of the cell, by inhibiting expression of a gene. The complex can be on the membrane of the cell or inside the cytoplasm, nucleus, or other organelle of the cell. Other terms sometimes used interchangeably with deliver include transfect, transfer, or transform.

BRIEF DESCRIPTION OF THE DRAWINGS

FIG. 1. Structure 1. Illustration of the chemical structures for cationic amphipathic compounds useful for delivery of siRNA to animal cells.

FIG. 2. Illustration of the chemical structure for Polyimidazolinium polymer imidazolinium subunits. A) Imidazolinium Subunit, B) 2-Imidazoline Subunit.

FIG. 3. Illustration of the chemical structure for: A) MC763, B) MC762, C) MC798.

FIG. 4. Illustration of the chemical structure for: A) MC765, B) MC764, C) MC798, D) MC774, E) MC775.

FIG. 5. Illustration of the chemical structure for: A) MC777, B) MC778, C) MC779.

FIG. 6. Illustration of the chemical structure for: A) MC780, B) MC781, C) MC782.

FIG. 7. Illustration of the chemical structure for: MC810, MC1069, MC1070.

FIG. 8. Illustration of the chemical structure for: MC1083, MC1086, MC1084.

DETAILED DESCRIPTION

Figure 9:
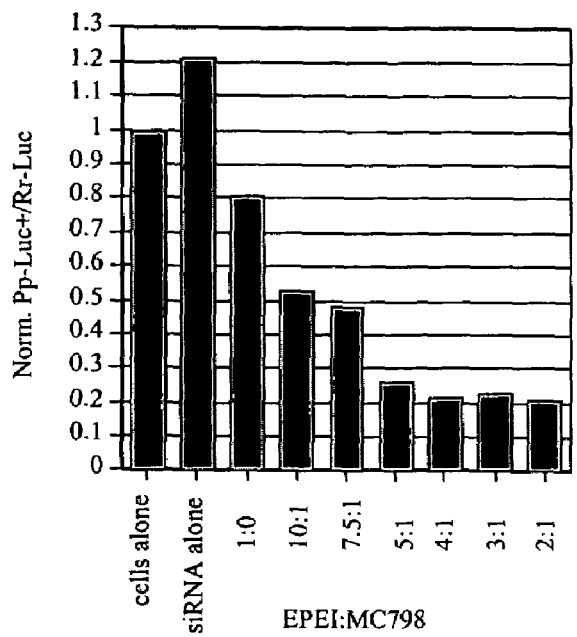
FIG. 9. MC798 addition to ePEI results in increased delivery of siRNA. Inhibition of luciferase activity in COS7 cells after delivery of siRNA with various ratios of ePEI and MC798.

The present invention describes cationic amphipathic compounds, and the methods of preparation thereof, that enhance delivery of a siRNA to an animal cell wherein the compounds have the general structures comprising the structures shown in FIG. 1, wherein $R_1$ and $R_2$ is selected from the group consisting of a C6 to C24 alkane, C6-C24 alkene, mono-, di-, or tri-substituted alkyl silane, cycloalkyl, sterol, steroid, appropriately substituted lipid, acyl segment of a fatty acid, hydrophobic hormone, or other similar hydrophobic group.

The compound is considered cationic because the molecule has on overall positive charge (zeta potential that is positive). The compound is considered amphipathic because the molecule contains one end that is hydrophilic while the other end is hydrophobic. Hydrophobic groups indicate in qualitative terms that the chemical moiety is water-avoiding. Typically, Hydrophobic groups indicate in qualitative terms that the chemical moiety is water-avoiding. Hydrocarbons are hydrophobic groups. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides, and groups containing amines, amides, alkoxy amides, carboxylic acids, sulfurs, or hydroxyls.

These amphipathic compounds are combined with a polycation and a siRNA to form a complex which is then associated with an animal for the purpose of delivering the siRNA to the cell. In another preferred embodiment, these amphipathic compounds may also be combined with other amphipathic compounds, such a lipids to form liposomes which are then used to delivery a siRNA to an animal cell.

The described compositions may be dried prior to use. The compositions may be dried with or without siRNA. The compositions are then reconstituted with cell culture media or other acceptable media for delivery of siRNA to cells. Examples of acceptable media include, but are not limited to, OptiMEM (Invitrogen), Dulbecco's modified Eagle's medium, and phosphate buffered saline. Cells are then added to the reconstituted compounds. If the compositions are dried without siRNA, the siRNA is added to the composition before adding cells.

The compositions are compatible with multi-well formats for delivery of siRNA to cells in vitro. Multiwell formats include cell culture plates that contain multiple wells for growing cells. Multiwell plates can be selected from the group comprising: 6-well plates, 12-well plates, 24-well plates, 96-well plates, and 384-well plates 864-well plates, and 1536-well plates. The described compositions can be dried in multiwell plates with or without siRNA. Such plates would allow high throughput screening using siRNA. Such plates could be used in screening libraries or arrays of siRNAs or in screening siRNA effects in response to different factors or compounds.

Also provided is a kit comprising a receptacle containing the compositions described for delivering siRNA to cell. Instructions for use are also provided with the kit. By the term instructions for use, it is meant a tangible expression describing the reagent concentration for at least one assay method, parameters such as the relative amount of reagent and sample to be admixed, maintenance time periods for reagent/sample admixtures, temperature, buffer conditions and the like. The receptacle may be a multiwell plate.

An siRNA is a nucleic acid that is a short, 15-50 base pairs and preferably 21-25 base pairs, double stranded ribonucleic acid. The term nucleic acid is a term of art that refers to a polymer containing at least two nucleotides. Natural nucleotides contain a deoxyribose (DNA) or ribose (RNA) group, a phosphate group, and a base. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the base such as, but not limited to, amines, alcohols, thiols, carboxylates, and alkylhalides. The term base encompasses any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. Nucleotides are the monomeric units of nucleic acid polymers and are linked together through the phosphate groups in natural polynucleotides. Natural polynucleotides have a ribose-phosphate backbone. Artificial or synthetic polynucleotides are polymerized in vitro and contain the same or similar bases but may contain a backbone of a type other than the natural ribose-phosphate backbone. These backbones include, but are not limited to: PNAs (peptide nucleic acids), phosphorothioates, phosphorodiamidates, morpholinos, and other variants of the phosphate backbone of natural polynucleotides.

The siRNA contains sequence that is identical or nearly identical to a portion of a gene. RNA may be polymerized in vitro, recombinant RNA, contain chimeric sequences, or derivatives of these groups. The siRNA may contain ribonucleotides, deoxyribonucleotides, synthetic nucleotides, or any suitable combination such that expression of the target gene is inhibited. The RNA is preferably double stranded, but may be single, triple, or quadruple stranded. An example of a single strand siRNA is an siRNA with a hairpin loop.

A delivered siRNA can stay within the cytoplasm or nucleus. The siRNA can be delivered to a cell to inhibit expression an endogenous or exogenous nucleotide sequence or to affect a specific physiological characteristic not naturally associated with the cell.

Protein refers herein to a linear series of greater than 2 amino acid residues connected one to another as in a polypeptide. A "therapeutic" effect of the protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, growth factors, clotting factors, anti-protease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood. Proteins on the membrane can have a therapeutic effect by providing a receptor for the cell to take up a protein or lipoprotein (e.g., low density lipoprotein receptor). Therapeutic proteins that stay within the cell ("intracellular proteins") can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, dystroglycans) and thus have a therapeutic effect in cardiomyopathies and musculoskeletal diseases (e.g., Duchenne's muscular dystrophy, limb-girdle disease). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors.

A siRNA can be delivered to a cell in order to produce a cellular change that is therapeutic. The delivery of siRNA or other genetic material for therapeutic purposes (the art of improving health in an animal including treatment or prevention of disease) is called gene therapy. The siRNA can be delivered either directly to the organism in situ or indirectly by transfer to a cell ex vivo that is then transplanted into the organism. Entry into the cell is required for the siRNA to block the production of a protein or to decrease the amount of a RNA. Diseases, such as autosomal dominant muscular dystrophies, which are caused by dominant mutant genes, are examples of candidates for treatment with therapeutic siRNA. Delivery of siRNA would block production of the dominant protein thereby lessening the disease.

A polycation means a polymer possessing net positive charge, for example poly-L-lysine hydrobromide, polyethylenimine, or histone. The polymeric polycation may contain monomer units that are charge positive, charge neutral, or charge negative, however, the net charge of the polymer must be positive. A polycation also means a non-polymeric molecule that contains two or more positive charges.

A DNA-binding protein is a protein that associates with nucleic acid under conditions described in this application and forms a complex with nucleic acid with a high binding constant. The DNA-binding protein can be used in an effective amount in its natural form or a modified form for this process. An "effective amount" of the polycation is an amount that will allow delivery of the siRNA to occur. In a preferred embodiment, the polycation is a polynucleotide-binding protein that is isolated from an animal tissue, such as calf thymus, or produced in recombinant form from *E. coli*. Preferably, the polynucleotide-binding protein is cationic such as a histone protein. Histone H1 protein is the preferred histone type and can be purchased from several suppliers (Sigma, Invitrogen, etc).

OTHER DEFINITIONS

Lipid—
Any of a diverse group of organic compounds that are insoluble in water, but soluble in organic solvents such as chloroform and benzene. Lipids contain both hydrophobic and hydrophilic sections. Lipids is meant to include complex lipids, simple lipids, and synthetic lipids.

Complex Lipids—
Complex lipids are the esters of fatty acids and include glycerides (fats and oils), glycolipids, phospholipids, and waxes.

Simple Lipids—
Simple lipids include steroids and terpenes.

Synthetic Lipids—
Synthetic lipids includes amides prepared from fatty acids wherein the carboxylic acid has been converted to the amide, synthetic variants of complex lipids in which one or more oxygen atoms has been substituted by another heteroatom (such as Nitrogen or Sulfur), and derivatives of simple lipids in which additional hydrophilic groups have been chemically attached. Synthetic lipids may contain one or more labile groups.

Fats—
Fats are glycerol esters of long-chain carboxylic acids. Hydrolysis of fats yields glycerol and a carboxylic acid—a fatty acid. Fatty acids may be saturated or unsaturated (contain one or more double bonds).

Oils—
Oils are esters of carboxylic acids or are glycerides of fatty acids.

Glycolipids—
Glycolipids are sugar containing lipids. The sugars are typically galactose, glucose or inositol.

Phospholipids—
Phospholipids are lipids having both a phosphate group and one or more fatty acids (as esters of the fatty acid). The phosphate group may be bound to one or more additional organic groups.

Wax—
Waxes are any of various solid or semisolid substances generally being esters of fatty acids.

Fatty Acids—
Fatty acids are considered the hydrolysis product of lipids (fats, waxes, and phosphoglycerides).

Polyimidazolinium—
A polyimidazolinium is a polymer (random copolymer, block copolymer, or other copolymer) containing one or more imidazolinium subunits. A polyimidazolium also means a homopolymer of the imidazolinium subunit. The imidazolinium subunit can be in the main chain of the polymer or as a side chain off of the polymer main chain. The polymer can be a net neutral polymer, a polycation, or a polyanion.

Imidazolinium (Imidazolinium Subunit FIG. 2A)—
In an imidazolinium (imidazolinium subunit), substituents R1, R2, R3, R4a, R4b, R5a, and R5b can independently be a hydrogen radical or a carbon radical with any substitution. The counterion (X) can be any counterion. Counterions include, but are not limited to chloride, bromide, iodide, and tosylate.

Poly-2-Imidazoline—
A poly-2-imidazoline is a polymer (random copolymer, block copolymer, or other copolymer) containing one or more imidazoline subunits. A poly-2-imidazoline also means a homopolymer of the 2-imidazoline subunit. The imidazoline subunit can be in the main chain of the polymer or as a side chain off of the polymer main chain. The polymer can be a net neutral polymer, a polycation, or a polyanion.

2-Imidazoline (2-Imidazoline Subunit, FIG. 2B):
In a 2-imidazoline (imidazoline subunit), substituents R1, R2, R4a, R4b, R5a, and R5b can independently be a hydrogen radical or a carbon radical with any substitution.

Complex—
Two molecules are combined, to form a complex through a process called complexation or complex formation, if the are in contact with one another through noncovalent interactions such as electrostatic interactions, hydrogen bonding interactions, and hydrophobic interactions.

Modification—
A molecule is modified, to form a modification through a process called modification, by a second molecule if the two become bonded through a covalent bond. That is, the two molecules form a covalent bond between an atom form one molecule and an atom from the second molecule resulting in the formation of a new single molecule. A chemical covalent bond is an interaction, bond, between two atoms in which there is a sharing of electron density. Modification also means an interaction between two molecules through a noncovalent bond. For example crown ethers can form noncovalent bonds with certain amine groups.

Salt—

A salt is any compound containing ionic bonds, that is bonds in which one or more electrons are transferred completely from one atom to another. Salts are ionic compounds that dissociate into cations and anions when dissolved in solution and thus increase the ionic strength of a solution.

Pharmaceutically Acceptable Salt—

Pharmaceutically acceptable salt means both acid and base addition salts.

Pharmaceutically Acceptable Acid Addition Salt—

A pharmaceutically acceptable acid addition salt is those salts which retain the biological effectiveness and properties of the free bases, and are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, trifluoroacetic acid, and the like.

Pharmaceutically Acceptable Base Addition Salt—

A pharmaceutically acceptable base addition salt is those salts which retain the biological effectiveness and properties of the free acids, and are not biologically or otherwise undesirable. The salts are prepared from the addition of an inorganic base or an organic base to the free acid. Salts derived from inorganic bases include, but are not limited to, sodium, potassium, calcium, lithium, ammonium, magnesium, zinc, and aluminum salts and the like. Salts derived from organic bases include, but are not limited to salts of primary secondary, and tertiary amines, such as methylamine, triethylamine, and the like.

Interpolyelectrolyte Complexes—

An interpolyelectrolyte complex is a noncovalent interaction between polyelectrolytes of opposite charge.

Charge, Polarity, and Sign—

The charge, polarity, or sign of a compound refers to whether or not a compound has lost one or more electrons (positive charge, polarity, or sign) or gained one or more electrons (negative charge, polarity, or sign).

Cell Targeting Signals—

Cell targeting signal (or abbreviated as the Signal) is defined in this specification as a molecule that modifies a biologically active compounds such as drug or nucleic acid and can direct it to a cell location (such as tissue) or location in a cell (such as the nucleus) either in culture or in a whole organism. By modifying the cellular or tissue location of the foreign gene, the function of the biologically active compound can be enhanced.

The cell targeting signal can be a protein, peptide, lipid, steroid, sugar, carbohydrate, (non-expressing) polynucleic acid or synthetic compound. The cell targeting signal enhances cellular binding to receptors, cytoplasmic transport to the nucleus and nuclear entry or release from endosomes or other intracellular vesicles.

Nuclear localizing signals enhance the targeting of the pharmaceutical into proximity of the nucleus and/or its entry into the nucleus. Such nuclear transport signals can be a protein or a peptide such as the SV40 large T Antigen NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS or long NLS's and. Other NLS peptides have been derived from M9 protein, nucleoplasmin, and c-myc.

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the biologically active compound with a cell. This can be accomplished by either increasing the binding of the compound to the cell surface and/or its association with an intracellular compartment, for example: ligands that enhance endocytosis by enhancing binding the cell surface. This includes agents that target to the asialoglycoprotein receptor by using asialoglycoproteins or galactose residues. Other proteins such as insulin, EGF, or transferrin can be used for targeting. Peptides that include the RGD sequence can be used to target many cells. Chemical groups that react with thiol or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

Interaction Modifiers—

An interaction modifier changes the way that a molecule interacts with itself or other molecules, relative to molecule containing no interaction modifier. The result of this modification is that self-interactions or interactions with other molecules are either increased or decreased. For example cell targeting signals are interaction modifiers with change the interaction between a molecule and a cell or cellular component. Polyethylene glycol is an interaction modifier that decreases interactions between molecules and themselves and with other molecules.

Linkages—

An attachment that provides a covalent bond or spacer between two other groups (chemical moieties). The linkage may be electronically neutral, or may bear a positive or negative charge. The chemical moieties can be hydrophilic or hydrophobic. Preferred spacer groups include, but are not limited to C1-C12 alkyl, C1-C12 alkenyl, C1-C12 alkynyl, C6-C18 aralkyl, C6-C18 aralkenyl, C6-C18 aralkynyl, ester, ether, ketone, alcohol, polyol, amide, amine, polyglycol, polyether, polyamine, thiol, thio ether, thioester, phosphorous containing, and heterocyclic. The linkage may or may not contain one or more labile bonds.

Bifunctional—

Bifunctional molecules, commonly referred to as crosslinkers, are used to connect two molecules together, i.e. form a linkage between two molecules. Bifunctional molecules can contain homo or heterobifunctionality.

Labile Bond—

A labile bond is a covalent bond that is capable of being selectively broken. That is, the labile bond may be broken in the presence of other covalent bonds without the breakage of other covalent bonds. For example, a disulfide bond is capable of being broken in the presence of thiols without cleavage of any other bonds, such as carbon-carbon, carbon-oxygen, carbon-sulfur, carbon-nitrogen bonds, which may also be present in the molecule. Labile also means cleavable.

Labile Linkage—

A labile linkage is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

pH-Labile Linkages and Bonds— pH-labile refers to the selective breakage of a covalent bond under acidic conditions (pH<7). That is, the pH-labile bond may be broken under acidic conditions in the presence of other covalent bonds without their breakage.

Amphiphilic and Amphipathic Compounds—

Amphipathic, or amphiphilic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Polymers—

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft. The main chain of a polymer is composed of the atoms whose bonds are required for propagation of polymer length. The side chain of a polymer is composed of the atoms whose bonds are not required for propagation of polymer length.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" [M. P. Stevens Polymer Chemistry: An Introduction New York Oxford University Press 1990]. Template polymerization can be used to form polymers from daughter polymers.

Step Polymerization:

In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed. Typically, step polymerization is done either of two different ways. One way, the monomer has both reactive functional groups (A and B) in the same molecule so that A—B yields —[A—B]—

Or the other approach is to have two difunctional monomers.

A—A+B—B yields —[A—A—B—B]—

Generally, these reactions can involve acylation or alkylation. Acylation is defined as the introduction of an acyl group (—COR) onto a molecule. Alkylation is defined as the introduction of an alkyl group onto a molecule.

If functional group A is an amine then B can be (but not restricted to) an isothiocyanate, isocyanate, acyl azide, N-hydroxysuccinimide, sulfonyl chloride, aldehyde (including formaldehyde and glutaraldehyde), ketone, epoxide, carbonate, imidoester, carboxylate, or alkylphosphate, arylhalides (difluoro-dinitrobenzene), anhydrides or acid halides, p-nitrophenyl esters, o-nitrophenyl pentachlorophenyl esters, or pentafluorophenyl esters. In other terms when function A is an amine then function B can be acylating or alkylating agent or amination.

If functional group A is a thiol, then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which a carbodiimide is used. Other additives may be utilized such as carbonyldiimidazole, dimethylaminopyridine, N-hydroxysuccinimide or alcohol using carbodiimide and dimethylaminopyridine.

If functional group A is a hydroxyl then function B can be (but not restricted to) an epoxide, oxirane, or an amine in which carbonyldiimidazole or N, N'-disuccinimidyl carbonate, or N-hydroxysuccinimidyl chloroformate or other chloroformates are used.

If functional group A is an aldehyde or ketone then function B can be (but not restricted to) an hydrazine, hydrazide derivative, amine (to form a imine or iminium that may or may not be reduced by reducing agents such as $NaCNBH_3$) or hydroxyl compound to form a ketal or acetal.

Yet another approach is to have one difunctional monomer so that

A—A plus another agent yields —[A—A]—.

If function A is a thiol group then it can be converted to disulfide bonds by oxidizing agents such as iodine ($I_2$) or $NaIO_4$ (sodium periodate), or oxygen ($O_2$). Function A can also be an amine that is converted to a thiol group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, thiol, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thio-ether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methacrylamide groups can undergo chain reaction, which can be radical, anionic, or cationic. Chain polymerization can also be accomplished by cycle or ring opening polymerization. Several different types of free radical initiators could be used that include peroxides, hydroxy peroxides, and azo compounds such as 2,2'-Azobis(-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrazine, heterocycles (like imidazole, pyridine, morpholine, pyrimidine, or pyrene. The amines could be pH-sensitive in that the $pK_a$ of the amine is within the physiologic range of 4 to 8. Specific amines include spermine, spermidine, N,N'-bis(2-aminoethyl)-1,3-propanediamine (AEPD), and 3,3'-Diamino-N,N-dimethyl-dipropylammonium bromide.

Monomers can also be hydrophobic, hydrophilic or amphipathic. Monomers can also be intercalating agents such as acridine, thiazole orange, or ethidium bromide.

Other Components of the Monomers and Polymers: The polymers have other groups that increase their utility. These groups can be incorporated into monomers prior to polymer formation or attached to the polymer after its formation. These groups include: Targeting Groups—such groups are used for targeting the polymer-nucleic acid complexes to specific cells or tissues. Examples of such targeting agents include agents that target to the asialoglycoprotein receptor by using asialoglycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Chemical groups that react with thiol or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Polyelectrolyte—

A polyelectrolyte, or polyion, is a polymer possessing more than one charge, i.e. the polymer contains groups that have either gained or lost one or more electrons. A polycation is a polyelectrolyte possessing net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polyelectrolyte containing a net negative charge. The polyanion can contain monomer units that are charge negative, charge neutral, or charge positive, however, the net charge on the polymer must be negative. A polyanion can also mean a non-polymeric molecule that contains two or more negative charges. The term polyelectrolyte includes polycation, polyanion, zwitterionic polymers, and neutral polymers. The term zwitterionic refers to the product (salt) of the reaction between an acidic group and a basic group that are part of the same molecule.

Steric Stabilizer—

A steric stabilizer is a long chain hydrophilic group that prevents aggregation of final polymer by sterically hindering particle to particle electrostatic interactions. Examples include: alkyl groups, PEG chains, polysaccharides, alkyl amines. Electrostatic interactions are the non-covalent association of two or more substances due to attractive forces between positive and negative charges.

Buffers—

Buffers are made from a weak acid or weak base and their salts. Buffer solutions resist changes in pH when additional acid or base is added to the solution.

Biological, Chemical, or Biochemical Reactions—

Biological, chemical, or biochemical reactions involve the formation or cleavage of ionic and/or covalent bonds.

Reactive—

A compound is reactive if it is capable of forming either an ionic or a covalent bond with another compound. The portions of reactive compounds that are capable of forming covalent bonds are referred to as reactive functional groups.

Steroid—

A steroid derivative means a sterol, a sterol in which the hydroxyl moiety has been modified (for example, acylated), or a steroid hormone, or an analog thereof. The modification can include spacer groups, linkers, or reactive groups.

Sterics—

Steric hindrance, or sterics, is the prevention or retardation of a chemical reaction because of neighboring groups on the same molecule.

EXAMPLES

1. Synthesis of Amphipathic Compounds

A. Synthesis of MC763: To a 25 ml flame dried flask was added oleoyl chloride (freshly distilled, 1.0 ml, 3.0 mmol, Aldrich Chemical Company) and lauroyl chloride (0.70 ml, 3.0 mmol, Aldrich Chemical Company) in 15 ml dichloromethane under $N_2$. The resulting solution was cooled to 0° C. in an ice bath. N,N-Diisopropylethylamine (1.1 ml, 6.1 mmol, Aldrich Chemical Company) was added followed by 1,4-bis(3-aminopropyl)piperazine (0.50 ml, 2.4 mmol, Aldrich Chemical Company). The ice bath was removed and the solution stirred at ambient temperature for 15 h. The solution was washed twice with 1N NaOH (10 ml), twice with water (10 ml), and concentrated under reduced pressure. Approximately 30% of the resulting residue was purified by semi-preparative HPLC on a Beta Basic Cyano column (150 Å, 5 μm, 250×21 mm, Keystone Scientific, Inc.) with acetonitrile/ $H_2O$/trifluoroacetic acid eluent. Three compounds were isolated from the column and verified by mass spectroscopy (Sciex API 150EX).

MC763 (MW=647.10, FIG. 3A)
MC762 (MW=564.95, FIG. 3B)
MC798 (MW=729.25, FIG. 3C)

B. Synthesis of MC765: To a 25 ml flame dried flask was added oleoyl chloride (freshly distilled, 1.0 ml, 3.0 mmol) and myristoyl chloride (0.83 ml, 3.0 mmol, Aldrich Chemical Company) in 15 ml dichloromethane under $N_2$. The resulting solution was cooled to 0° C. in an ice bath. N,N-Diisopropylethylamine (1.1 ml, 6.1 mmol) was added followed by 1,4-bis(3-aminopropyl)piperazine (0.50 ml, 2.4 mmol). The ice bath was removed and the solution stirred at ambient temperature for 15 h. The solution was washed twice with 1N NaOH (10 ml), twice with water (10 ml), and concentrated under reduced pressure. Approximately 30% of the resulting residue was purified by semi-preparative HPLC on a Beta Basic Cyano column with acetonitrile/H2O/trifluoroacetic acid eluent. Three compounds were isolated from the column and verified by mass spectroscopy.

MC765 (MW=675.15, FIG. 4A)
MC764 (MW=621.05, FIG. 4B)
MC798 (MW=729.25, FIG. 4C)

C. Synthesis of MC774. To a solution of 1,4-bis(3-aminopropyl)piperazine (10 μl, 0.049 mmol, Aldrich Chemical Company) in dichloromethane (1 ml) cooled to 0° C., was added decanoyl chloride (25 μl, 0.12 mmol, Aldrich Chemical Company) and N,N-Diisopropylethylamine (21 μl, 0.12 mmol). After 30 min, the solution was allowed to warm to ambient temperature. After 12 hrs, the solution was washed with water (2×2 ml), and concentrated under reduced pressure to afford MC774 (21.6 mg, 87%, MW=508.83, FIG. 4D) of sufficient purity by TLC.

D. Synthesis of MC775: To a solution of 1,4-bis(3-aminopropyl)piperazine (10 μl, 0.049 mmol) in dichloromethane (1 ml), was added palmitoleic acid (30.8 mg, 0.12 mmol, Aldrich Chemical Company), N,N-Diisopropylethylamine (21 μl, 0.12 mmol), and dicyclohexylcarbodiimide (25 mg, 0.12 mmol). After 12 h, the solution was filtered and washed with water (2×2 ml), and concentrated under reduced pressure to afford MC775 (26.5 mg, 81%, MW=673.14, FIG. 4E) of sufficient purity by TLC.

E. Synthesis of MC777, MC778, and MC779: To a solution of benzotriazole-1-yl-oxy-tris-pyrrolidino-phosphonium hexafluorophosphate (PyBOP, 1.300 g, 2.500 mmol, Nova-Biochem) in dichloromethane (8 ml) was added thioctic acid (0.248 g, 1.20 mmol, Aldrich Chemical Company) and linolenic acid (365 μl, 1.20 mmol, Aldrich Chemical Company). To the resulting solution was added 1,4-bis(3-aminopropyl)-piperazine (206 μl, 1.00 mmol) followed by N,N-Diisopropylethylamine (610 μl, 3.5 mmol). After 16 h at ambient temperature, the solution was washed with water (2×20 ml), and concentrated under reduced pressure to afford 1.800 g of crude material. A 85 mg portion of the crude material was dissolved in 2 ml of acetonitrile (0.1% trifluoroacetic acid)/1 ml of water (0.1% trifluoroacetic acid), and purified by reverse phase HPLC (10-90% B over 40 min) on a Beta Basic Cyano column to afford 31.8 mg MC777 (MW=576.97, FIG. 5A), 1.3 mg MC778 (MW=649.07, FIG. 5B), and 1.5 mg MC779 (MW=721.18, FIG. 5C).

F. Synthesis of MC780, MC781, and MC782: Compounds MC780, MC781, and MC782 were made using a similar synthesis to compounds MC777, MC778, and MC779, from the reaction of 1,4-bis(3-aminopropyl)-piperazine, trans-retinoic acid, and eicosenoic acid. The crude material from the synthesis was dissolved in 2 ml of acetonitrile (0.1% trifluoroacetic acid)/1 ml of water (0.1% trifluoroacetic acid), and purified by reverse phase HPLC (10-90% B over 40 min) on a Beta Basic Cyano column to afford 7.1 mg MC780 (MW=765.20, FIG. 6A), 13.0 mg MC781 (MW=775.28, FIG. 6B), and 18.0 mg MC782 (MW=785.36, FIG. 6C).

G. Synthesis of Polysilazanes: General experimental: The polyamine is dissolved in DMF to a concentration between 20 and 50 mg/ml. In a separate vessel, the chlorosilane is dissolved in THF to a concentration between 20 and 50 mg/ml. The appropriate amount of the chlorosilane solution (based on the molar ratio of amine residues to be modified) is added to the solution of the polyamine with mixing, resulting in the formation of a white solid. Water is added to the reaction vessel to a final concentration between 1 and 10 mg/ml based on the polyamine immediately prior to use. A solid support base may be included such as diisopropylaminomethyl polystyrene, which is removed by filtration or centrifugation of the final solution. According to this general experimental procedure, the following compounds were prepared:

TABLE 1

Polysilazane polymers

| chlorosilane | polyamine (percent modification of amines-MC compound number) | | | | | |
|---|---|---|---|---|---|---|
| | PEI-800 | PEI-1800 | PEI-10k | brPEI-25k | lPEI-25k | E-PEI |
| Cl—Si(CH₃)(CH₃)—Cl | 40-MC652<br>60-MC653 | 40-MC662<br>60-MC663<br>80-MC694 | 20-MC642<br>30-MC643 | 10-MC622<br>20-MC623<br>40-MC681 | 10-MC630<br>20-MC631 | 40-MC681 |

TABLE 1-continued

Polysilazane polymers

| chlorosilane | polyamine (percent modification of amines-MC compound number) | | | | | |
|---|---|---|---|---|---|---|
| | PEI-800 | PEI-1800 | PEI-10k | brPEI-25k | lPEI-25k | E-PEI |
| tBu—Si(Cl)(Cl)—tBu | 40-MC654 | 40-MC664 | 20-MC644 | 10-MC624 | 10-MC632 | |
| | 60-MC655 | 60-MC665 | 30-MC645 | 20-MC625 | 20-MC633 | |
| Ph—Si(Cl)(Cl)—Ph | 40-MC656 | 40-MC666 | 20-MC646 | 10-MC626 | 10-MC634 | |
| | 60-MC657 | 60-MC667 | 30-MC647 | 20-MC627 | 20-MC635 | |
| Cl-Si(CH$_3$)(CH$_3$)-Si(CH$_3$)(CH$_3$)-Cl | 10-MC616 | 10-MC618 | 20-MC650 | 10-MC607 | 10-MC609 | |
| | 20-MC617 | 20-MC619 | 30-MC651 | 20-MC608 | 20-MC610 | |
| | 30-MC660 | 40-MC670 | | | | |
| | 60-MC661 | 60-MC671 | | | | |
| Cl-Si(iPr)(iPr)-O-Si(iPr)(iPr)-Cl | 40-MC658 | 40-MC668 | 20-MC648 | 10-MC628 | 10-MC636 | |
| | 60-MC659 | 60-MC669 | 30-MC649 | 20-MC629 | 20-MC637 | |

Reagents:
brPEI-800, brPEI-1800; Polyethylenimine (base polymer average M$_w$ ca. 800,1800), Aldrich Chemical Company.
PEI-10k; Polyethylenimine (base polymer average M$_w$ ca. 10,000), Polysciences, Inc.
brPEI-25k; branched Polyethylenimine (base polymer average M$_w$ ca. 25000), Aldrich Chemical Company.
lPEI-25k; linear-Polyethylenimine (base polymer average M$_w$ ca. 25,000), Polysciences, Inc.
E-PEI; Polyethylenimine, 80-ethoxylated (base polymer average M$_w$ ca. 50,000), Aldrich Chemical Company.
Dichlorodimethylsilane, Di-tert-butyldichlorosilane, Dichlorodiphenylsilane, Aldrich Chemical Company.
1,1,4,4-Tetramethyl-1,4-dichlordisilethylene, 1,3-Dichlorotetraisopropyldisiloxane, United Chemical Technologies, Inc.
Diisopropylaminomethyl polystyrene, Fluka Chemical Company.

H. Synthesis of MC810 (FIG. 7). To a solution of palmitoleic acid (cis-9-hexadecanoic acid, 2.00 g, 7.87 mmol, Aldrich Chemical Company) in dichloromethane (75 mL), was added oxalyl chloride (1.72 mL, 19.7 mmol, Aldrich Chemical Company) dropwise under nitrogen. After 16 hrs, the solution was concentrated under reduced pressure (aspirator) and then placed under high vacuum to afford palmitoleoyl chloride.

To a solution of 1,4-bis(2-hydroxyethyl)piperazine (575 mg, 3.30 mmol, Aldrich Chemical Company) in THF (18 mL), was added diisopropylethylamine (2.3 mL, 13.2 mmol, Aldrich Chemical Company) and a catalytic amount of 4-(dimethylamino)pyridine (DMAP, Aldrich Chemical Company), and the resulting solution was cooled to −20° C. To this solution was added a solution of palmitoleoyl chloride (7.87 mmol) in THF (12 mL), dropwise under nitrogen. The cooling bath was removed, and the solution was allowed to warm to ambient temperature. After 30 min, acetonitrile (9 mL) was added. After 2 hrs the reaction appeared complete by TLC. The solution was concentrated under reduced pressure (aspirator). The resulting residue was dissolved in ethyl acetate and washed with water (2×20 mL), 1N HCl (20 mL), 1N NaOH, and brine (20 mL), dried (Na$_2$SO$_4$), filtered, and concentrated under reduced pressure (aspirator) and high vacuum to afford 1.03 g (48.4%) MC810 as a yellow oil. M+1=647.6 (PE Sciex API 150EX). Analytical HPLC (Beta Basic Cyano column, Keystone Scientific, Inc.) indicated sample purity of 96%.

I. Synthesis of MC1069 (FIG. 7). By similar procedures as detailed in example 1, MC1069 was prepared from the reaction of 1,4-bis(2-hydroxyethyl)piperazine and lauroyl chloride (dodecanoyl chloride). The product was isolated in 10% yield following crystallization from acetonitrile, mp=42° C. (M+1=539.6, PE Sciex API 150EX, 100% by analytical HPLC, Beta Basic Cyano column, Keystone Scientific, Inc.).

J. Synthesis of MC1070 (FIG. 7). By similar procedures as detailed in example 1, MC1070 was prepared from the reaction of 1,4-bis(2-hydroxyethyl)piperazine and myristoyl chloride (tetradecanoyl chloride). The product was isolated in 67% yield following crystallization from acetonitrile, mp=47° C. (M+1=595.8, PE Sciex API 150EX, 100% by analytical HPLC, Beta Basic Cyano column, Keystone Scientific, Inc.).

K. Synthesis of MC1083 and MC1086 (FIG. 8). By similar procedures as detailed in example 1, MC1083 was prepared from the reaction of 1,4-bis(2-hydroxyethyl)piperazine and oleoyl chloride (prepared from the reaction of oleic acid (cis-9-octadecenoic acid) and oxalyl chloride). The product was isolated in 36% yield as a yellow oil following purification by flash column chromatography on silica gel (3.5% dichloromethane/methanol eluent), M+1=703.6 (PE Sciex API 150EX), 100% by analytical HPLC (Beta Basic Cyano column, Keystone Scientific, Inc.). An impure fraction of MC1086 (one tailed derivative) was also isolated from the flash column, 64% by analytical HPLC (Beta Basic Cyano column, Keystone Scientific, Inc.), M+1=439.4 (PE Sciex API 150EX).

L. Synthesis of MC1084 (FIG. 8). To a solution of 1,4-bis (2-hydroxyethyl)piperazine (400 mg, 2.29 mmol, Aldrich Chemical Company) in THF (25 mL), was added imidazole (392 mg, 5.75 mmol, Aldrich Chemical Company) and chlorodimethyloctadecylsilane (2.00 g, 5.75 mmol, Aldrich Chemical Company) under nitrogen, and the resulting solution was stirred at ambient temperature. After 16 hrs, the mixture was concentrated under reduced pressure (aspirator), and the resulting residue was dissolved in ethyl acetate and washed with brine (3×20 mL), dried ($Na_2SO_4$), filtered, and concentrated under reduced pressure aspirator) to afford 1.50 grams of MC1084 as a white solid of sufficient purity, One spot by TLC (10% dichloromethane/methanol eluent), 100% by analytical HPLC (Beta Basic Cyano column, Keystone Scientific, Inc.), M+1=795.8 (PE Sciex API 150EX).

2. Delivery of siRNA to Animal Cells In Vitro

Use of Reporter Genes: A marker or reporter gene is a polynucleotide that encodes a gene product that can be easily assayed, such as firefly luciferase or green fluorescent protein (GFP). The presence of the product of the marker gene indicates that the cell is transfected and the amount of the product indicates the efficiency of the transfection process. The luciferase reporter gene, in conjunction with siRNA delivery methods, was used in our studies to quantitatively determine the efficiency of siRNA delivery.

Preparation of Transfection Complexes: The compositions, or ternary complexes, are prepared by mixing the polynucleotide with one or more amphipathic compounds and an effective amount of a polycation. In one preferred embodiment, the siRNA is mixed first with the polycation in serum-free media or other non-toxic solution and the amphipathic compound is then added to the mixture. The mixture containing the ternary complex of siRNA, polycation and amphipathic compound is then added to the cells. In another preferred embodiment, the amphipathic compound is mixed first with the polycation in solution and then the siRNA is added to the mixture. The mixture containing the ternary complex of siRNA, polycation and amphipathic compound is then added to the cells.

A. Delivery of siRNA to mammalian ATCC COS7 cells. COS7 cells were maintained in Dulbecco's Modified Eagle Medium supplemented with 10% fetal bovine serum. All cultures were maintained in a humidified atmosphere containing 5% $CO_2$ at 37° C. Approximately 24 hours prior to transfection, cells were plated at an appropriate density in a T75 flask and incubated overnight. At 50% confluency, cells were initially transfected with pGL-3-control (firefly luciferase, Promega, Madison Wis.) and pRL-SV40 (sea pansy luciferase, Promega, Madison, Wis.) using TransIT-LT1 transfection reagent according to the manufacturer's recommendations (Mirus Corporation, Madison, Wis.). 15 µg pGL-3-control and 50 ng pRL-SV40 were added to 45 µl TransIT-LT1 in 500 µl Opti-MEM (Invitrogen) and incubated 5 min at RT. DNA complexes were then added to cells in the T75 flask and incubated 2 h at 37° C. Cells were washed with PBS, harvested with trypsin/EDTA, suspended in media, plated into a 24-well plate with 250 µl DMEM+10% serum and incubated 2 h at 37° C. siRNA-Luc+ (Pharmacon), 0.6 pmol, was then combined with the indicated delivery agent in 100 µl Opti-MEM per well, incubated 5 min at RT and added to cells at 37° C.

The pGL-3-control plasmid contains the firefly luc+ coding region under transcriptional control of the simian virus 40 enhancer and early promoter region. The pRL-SV40 plasmid contains the coding region for *Renilla reniformis*, sea pansy, luciferase under transcriptional control of the Simian virus 40 enhancer and early promoter region.

Single-stranded, gene-specific sense and antisense RNA oligomers with overhanging 3' deoxynucleotides were prepared and purified by PAGE (Dharmacon, LaFayette, Colo.). The two complementary oligonucleotides, 40 µM each, are annealed in 250 µl 100 mM NaCl/50 mM Tris-HCl, pH 8.0 buffer by heating to 94° C. for 2 minutes, cooling to 90° C. for 1 minute, then cooling to 20° C. at a rate of 1° C. per minute. The resulting siRNA was stored at −20° C. prior to use.

The sense oligonucleotide, with identity to the luc+ gene in pGL-3-control, had the sequence: 5'-rCrUrUrArCrGrCrUr-GrArGrUrArCrUrUrCrGrATT-3' (SEQ ID 1), corresponding to positions 155-173 of the luc+ reading frame. The letter "r" preceding a nucleotide indicates that the nucleotide is a ribonucleotide. The antisense oligonucleotide, with identity to the luc+ gene in pGL-3-control, had the sequence: 5'-rUrCr-GrArArGrUrArCrUrCrArGrCrGrUrArA-rGTT-3' (SEQ ID 2) corresponding to positions 173-155 of the luc+ reading frame in the antisense direction. The letter "r" preceding a nucleotide indicates that the nucleotide is a ribonucleotide. The annealed oligonucleotides containing luc+ coding sequence are referred to as siRNA-luc+.

Cells were harvested after 24 h and assayed for luciferase activity using the Promega Dual Luciferase Kit (Promega). A Lumat LB 9507 (EG&G Berthold, Bad-Wildbad, Germany) luminometer was used. The amount of luciferase expression was recorded in relative light units. Numbers were then adjusted for control sea pansy luciferase expression and are expressed as the percentage of firefly luciferase expression in the absence of siRNA. Numbers are the average for at least two separate wells of cells.

The results in FIG. 9 show that addition of the amphipathic compound, MC798, significantly enhances delivery of siRNA when combined with ePEI. Maximum delivery is achieved when the PEI/MC798 ratio is 4:1 (wt/wt).

TABLE 2

Delivery of siRNA-Luc+ to pGL3-control transfected COS7 cells with ePEI:amphipathic compound formulations.

| | amphipathic compound | ratio | PEI (µg) | siRNA (nM) | Luciferase Activity |
|---|---|---|---|---|---|
| none | | | | 0 | 1.000 |
| ePEI | MC798 | 4:1 | 6 | 0 | 0.751 |
| | | 4:1 | 6 | 1 | 0.105 |
| ePEI | MC762 | 3:1 | 6 | 1 | 0.300 |
| | | 4:1 | 6 | 1 | 0.187 |
| ePEI | MC763 | 3:1 | 6 | 1 | 0.162 |
| | | 4:1 | 6 | 1 | 0.176 |
| | | 4:1 | 8 | 1 | 0.161 |
| ePEI | MC762 | 3:1 | 6 | 1 | 0.174 |
| | | 4:1 | 6 | 1 | 0.278 |
| ePEI | MC765 | 3:1 | 6 | 1 | 0.166 |
| | | 4:1 | 6 | 1 | 0.126 |
| | | 4:1 | 8 | 1 | 0.218 |
| PEI | | | 6 | 0 | 0.143 |
| | | | 6 | 1 | 0.290 |

The results demonstrate the effective delivery of siRNA to COS7 cells using the indicated compositions.

Figure 10:
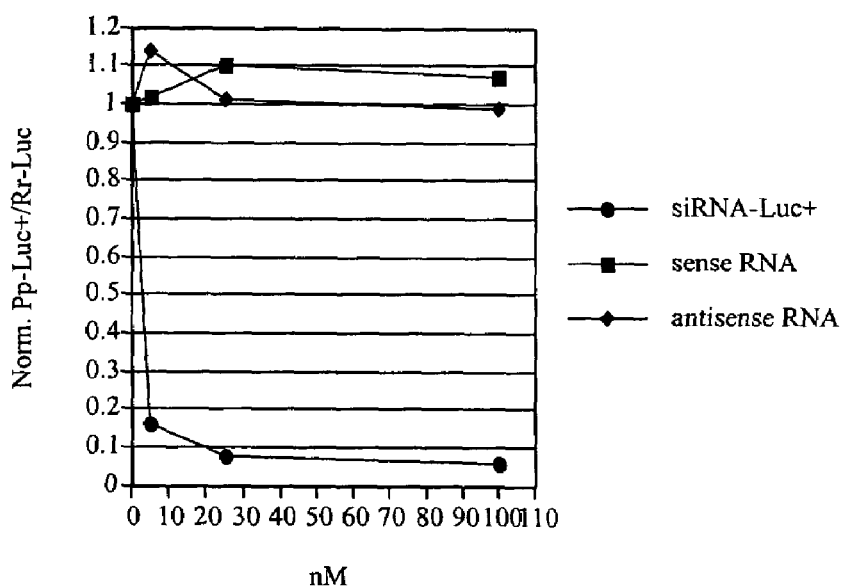
FIG. 10. Delivery of siRNA-Luc+ using ePEI:MC798 (4:1) results in strong and specific inhibition of Luc+ target gene expression in COS-7 cells in culture. The degree of inhibition of Luc+ by low concentrations of siRNA-Luc+ (0-1 nM) indicated an $IC_{50}$ of approximately 0.18 nM.

B. Ethoxylated-PEI/MC798 mediated siRNA delivery is highly effective in inhibiting expression of target genes in mammalian cells in culture: We performed siRNA-Luc+ titrations in transiently transfected COS-7 cells to determine the $IC_{50}$ of siRNA-Luc+. Results indicate that the concentration of siRNA required to inhibit target Luc+ expression by 50% is approximately 0.18 nM (FIG. 10). This concentration is at least 100-fold less than that required for even the most effective antisense molecules [Sharp 2001]. Maximal inhibition by siRNA-Luc+ occurred between 25 and 100 nM and was nearly 95%. This is quite remarkable given the high level of expression afforded by the SV-40 enhancer contained in the plasmids used to drive luciferase expression. No inhibition was observed when either the sense or antisense RNA strand of siRNA-Luc+ (FIG. 10) or when an siRNA targeted to sequences in the plasmid backbone was delivered (data not shown). These results indicate that siRNA is a highly effective reagent for inhibiting specific gene expression.

Figure 11:
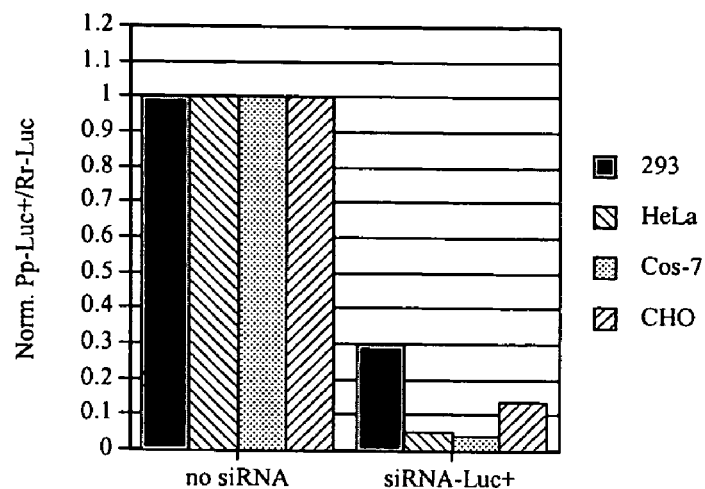
FIG. 11. ePEI/MC798 mediated delivery of siRNA results in strong inhibition of Luc+ expression in a variety of mammalian cell lines even at low siRNA concentration (1 nM).

C. Ethoxylated-PEI/MC798 is effective in delivering siRNA to multiple cell types. The effectiveness of siRNA was also tested in other mammalian cell lines transiently transfected with luciferase expression plasmids. Delivery of siRNA-Luc+ at 1 nM concentration to 293, HeLa, and CHO cells resulted in 70%, 94% and 87% inhibition, respectively, of the firefly luciferase target gene (FIG. 11). It is reasonable to expect that use of higher concentrations of siRNA would lead to even greater levels of inhibition. Experiments performed on mouse 3T3 cells stably transformed with a plasmid encoding the wild type version of firefly luciferase showed a 78% reduction in luciferase activity after delivery of 1 nM siRNA-Luc. Together these results indicate that siRNA is highly effective at inhibiting gene expression in both transiently and stably transformed mammalian cell lines.

D. Delivery of RNA oligo to HeLa-luc cells: The delivery of RNA oligo for a positive readout was also conducted. A commercially-available HeLa cell line that carries an integrated luciferase gene with a mutant splice site was employed. This mutant splice site results in production of a mRNA coding for a truncated inactive luciferase protein. The blocking RNA base pairs to and thus blocks this splice site, thereby enabling expression of the full-length active enzyme. Thus, the luciferase activity in this cell line is directly proportional to the amount of RNA delivered.

HeLa Luc/705 cells (Clontech Laboratories, Palo Alto, Calif.) were grown in as the standard HeLa cells. The cells were plated in 24-well culture dishes at a density of 3×10$^6$ cells/well and incubated for 24 hours. Media were replaced with 1.0 ml DMEM containing 2.5 nmol RNA oligo (2' OMe CCU CUU ACC UCA GUU ACA AUU UAU A (SEQ ID 3), TriLink BioTechnologies, San Diego, Calif.) and polycation/amphipathic compound. The cells were incubated for 4 hours in a humidified, 5% CO$_2$ incubator at 37° C. The media was then replaced with DMEM containing 10% fetal bovine serum. The cells were then incubated for an additional 48 h. The cells were then harvested and the lysates were then assayed for luciferase expression as previously reported using a Lumat LB 9507 (EG&G Berthold, Bad-Wildbad, Germany) luminometer [Wolff, 1990].

TABLE 4

Delivery of RNA-Oligo to HeLa-Luc cells with polycation:amphipathic compound formulations.

| polycation | amphipathic compound | ratio | µg polycation | RNA nM | RLU |
|---|---|---|---|---|---|
| None | | | | 0 | 868 |
| ePEI | MC798 | 3:1 | 5.0 | 2.5 | 2594 |
| | | 3:1 | 7.5 | 2.5 | 5221 |
| | | 3:1 | 10.0 | 2.5 | 8141 |
| | | 4:1 | 5.0 | 2.5 | 5053 |
| | | 4:1 | 7.5 | 2.5 | 27966 |
| | | 4:1 | 10.0 | 2.5 | 29582 |
| MC681 | | | 7.5 | 2.5 | 12798 |
| | | | 10.0 | 2.5 | 12533 |
| | | | 12.5 | 2.5 | 8188 |

TABLE 4-continued

Delivery of RNA-Oligo to HeLa-Luc cells with polycation:amphipathic compound formulations.

| polycation | amphipathic compound | ratio | µg polycation | RNA nM | RLU |
|---|---|---|---|---|---|
| MC681 | MC798 | 3:1 | 5.0 | 2.5 | 10806 |
| | | 3:1 | 7.5 | 2.5 | 9709 |
| | | 4:1 | 7.5 | 2.5 | 25702 |
| | | 4:1 | 10.0 | 2.5 | 14765 |
| | | 4:1 | 12.5 | 2.5 | 9200 | ePEI and MC681 with MC798 Show Delivery of the RNA Oligo to HeLa-Luc Cells.

Figure 12:
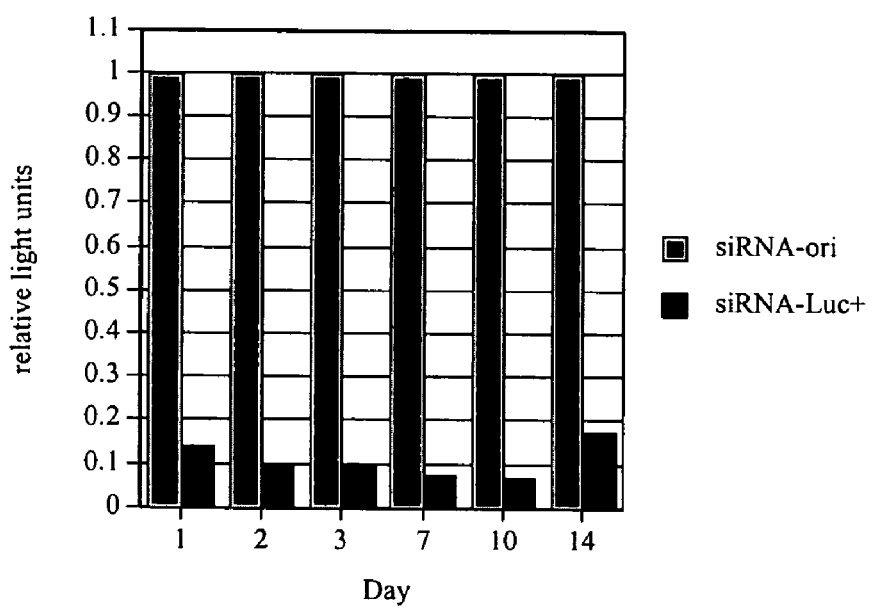
FIG. 12. Single application of TransIT-TKO delivered siRNA-Luc results in long-term inhibition of Luciferase expression. The data are normalized to cells receiving the control, siRNA-ori.

E. SiRNA mediated inhibition of a chromosomally integrated reporter gene: Ideally, the inhibitory effect of siRNA on target gene expression would be complete and long-lasting and work well on endogenous genes. These characteristics would enable straightforward analysis of gene function without the complications that can arise from interpreting data after only partial or short-term inhibition. In the previous examples we showed data that indicate that 95% inhibition can be achieved in cells lines transiently transfected with reporter genes. In order to determine if a chromosomally integrated gene (i.e. stably transfected) can be inhibited we performed an experiment using mouse NIH3T3 cells stably transfected with an expression plasmid encoding the wild type version of the firefly luciferase gene. EPEI+MC798 (TransIT-TKO) was used to deliver siRNA-Luc (or the control siRNA-ori to cells in replicate wells) at a final concentration of 25 nM. Controls included cells receiving TransIT-TKO alone and untreated cells. The media was changed and the cells split every 4 days during the course of the experiment. Cells from replicate wells were harvested on days 1, 2, 3, 7, 10 and 14 after transfection and assayed for Luciferase activity. Results, shown in FIG. 12, indicate that siRNA-Luc inhibition of Luciferase expression was in the 80-95% range on each day assayed. The levels of Luciferase activity in cells transfected with control siRNA or treated with TransIT-TKO alone were not significantly different than those in untreated cells. These results indicate that siRNA-mediated RNAi is highly effective and long lasting in these cultured cells, a result that is consistent with RNAi observed in studies performed on mouse oocytes where RNAi was observed over a 50 to 100-fold increase in cells mass 50, 51.

F. siRNA mediated inhibition of endogenous gene expression (nuclear lamin A/C) using EPEI and MC798: EPEI+ MC798 (TransIT-TKO) was used to deliver siRNA-Luc [or the control siRNA-ori to CHO (Chinese hamster ovary) cells in replicate wells] at a final concentration of 25 nM. Controls included cells receiving TransIT-TKO alone and untreated cells. The media was changed and the cells split every 4 days during the course of the experiment. Cells from replicate wells were harvested 2 days after transfection and total cellular protein was purified. Aliquots of protein from cells transfected with siRNA targeted for lamin A/C (and control siRNA) were run on a SDS-PAGE (3-12% gradient gel) and electrotransferred to nylon membranes. Protein expression of nuclear lamin A/C was quantitated via western blot analysis (anti-mouse lamin A/C) Results indicate that siRNA-lamin A/C inhibition of nuclear lamin expression was in the 80-95% range on the day assayed. The levels of lamin A/C in cells transfected with control siRNA or treated with TransIT-TKO alone were not significantly different than those in untreated cells. These results indicate that siRNA-mediated RNAi is highly effective in inhibiting expression of an endogenous cellular gene.

3. A. Polyvinylamine/MC798 is Effective in Delivering siRNA to Mammalian Cells CHO-luc cells, which contain an integrated luciferase gene, were maintained in medium supplemented with 0.5 mg/ml Geneticin (G418 Sulfate, Invitrogen). Approximately 24 h prior to transfection, cells were plated at an appropriate density in 24-well plates and incubated overnight. Cultures were maintained in a humidified atmosphere containing 5% $CO_2$ at 37° C. The indicated amount of GL3 siRNA was then combined with the indicated amount of polyvinylamine (pVA) or pVA+MC798 in 100 μl Opti-MEM per well, incubated 5 min at RT and added to cells at 37° C. All polyvinylamine containing solutions contained 2 mg/ml pVA polymer. Ratios for pVA:MC798 are given as weight:weight. Cells were harvested after 24 h and assayed for luciferase activity using a Lumat LB 9507 (EG&G Berthold, Bad-Wildbad, Germany) luminometer. The amount of luciferase expression was recorded in relative light units. Numbers were then adjusted for control cells and are expressed as the percentage of firefly luciferase expression in the absence of siRNA or in cells treated with polycation and MC798 alone. Numbers are the average for at least two separate wells. pVA+MC798 was efficient in delivery of siRNA to mammalian cells in vitro and exhibited similar or less toxicity compared to ePEI (Tables 5, 6, 7).

TABLE 5

Delivery of GL3 siRNA to CHO-Luc cells using the cationic polymer polyvinylamine.

| pVA (fraction) | pVA (μg) | siRNA (nM) | Total Luciferase Activity | Relative Luciferase Activity |
| --- | --- | --- | --- | --- |
| none | 0 | 0 | 1980828 | 1.000 |
|  | 2 | 10 | 902045 | 0.455 |
| unfractionated | 3 | 10 | 645238 | 0.326 |
|  | 4 | 10 | 526627 | 0.266 |
|  | 2 | 10 | 859993 | 0.434 |
| fraction 1 | 3 | 10 | 603525 | 0.305 |
|  | 4 | 10 | 431610 | 0.218 |
|  | 2 | 10 | 713075 | 0.360 |
| fraction 2 | 3 | 10 | 644068 | 0.325 |
|  | 4 | 10 | 482227 | 0.243 |
|  | 2 | 10 | 1084194 | 0.547 |
| fraction 3 | 3 | 10 | 762195 | 0.385 |
|  | 4 | 10 | 435304 | 0.220 |
|  | 2 | 10 | 1199180 | 0.605 |
| fraction 4 | 3 | 10 | 1092150 | 0.551 |
|  | 4 | 10 | 804362 | 0.406 |
|  | 2 | 10 | 1859924 | 0.939 |
| fraction 5 | 3 | 10 | 1576194 | 0.796 |
|  | 4 | 10 | 1270424 | 0.641 |

TABLE 6

Delivery of GL3 siRNA to CHO-Luc cells using polyvinylamine fraction 4:MC798 amphipathic compound formulations.

| pVA:MC798 ratio | μl per well | siRNA nM | Total Luciferase activity | Relative Luciferase Activity |
| --- | --- | --- | --- | --- |
| none | 0 | 0 | 4219527 |  |
| 3:1 | 1 | 0 | 3553454 | 1.000 |
|  |  | 10 | 1935402 | 0.545 |

TABLE 6-continued

Delivery of GL3 siRNA to CHO-Luc cells using polyvinylamine fraction 4:MC798 amphipathic compound formulations.

| pVA:MC798 ratio | μl per well | siRNA nM | Total Luciferase activity | Relative Luciferase Activity |
| --- | --- | --- | --- | --- |
|  | 2 | 0 | 3341685 | 1.000 |
|  |  | 10 | 661694 | 0.198 |
|  | 3 | 0 | 882682 | 1.000 |
|  |  | 10 | 435151 | 0.493 |
|  | 4 | 0 | 399545 | 1.000 |
|  |  | 10 | 70106 | 0.176 |
| 4:1 | 1 | 0 | 3229197 | 1.000 |
|  |  | 10 | 1469206 | 0.750 |
|  | 2 | 0 | 1957856 | 1.000 |
|  |  | 10 | 895387 | 0.457 |
|  | 3 | 0 | 760075 | 1.000 |
|  |  | 10 | 156727 | 0.206 |
|  | 4 | 0 | 233582 | 1.000 |
|  |  | 10 | 47368 | 0.212 |
| 5:1 | 1 | 0 | 3645432 | 1.000 |
|  |  | 10 | 1588305 | 0.436 |
|  | 2 | 0 | 2345214 | 1.000 |
|  |  | 10 | 713392 | 0.304 |
|  | 3 | 0 | 804753 | 1.000 |
|  |  | 10 | 228877 | 0.284 |
|  | 4 | 0 | 197065 | 1.000 |
|  |  | 10 | 56131 | 0.285 |

TABLE 7

Delivery of varying amount of GL3 siRNA to CHO-Luc cells using polyvinylamine fraction 4/5:MC798 amphipathic compound formulations

| pVA:MC798 ratio | μl per well | siRNA nM | Relative Luciferase Activity |
| --- | --- | --- | --- |
| fraction 4 | | | |
| 4:1 | 1.25 | 0 | 1.000 |
|  |  | 0.10 | 0.648 |
|  |  | 0.5 | 0.535 |
|  |  | 1 | 0.390 |
|  |  | 5 | 0.299 |
|  |  | 10 | 0.241 |
|  |  | 25 | 0.182 |
| 5:1 | 1.25 | 0 | 1.000 |
|  |  | 0.10 | 0.959 |
|  |  | 0.5 | 0.766 |
|  |  | 1 | 0.834 |
|  |  | 5 | 0.533 |
|  |  | 10 | 0.456 |
|  |  | 25 | 0.307 |
| fraction 5 | | | |
| 4:1 | 1.25 | 0 | 1.000 |
|  |  | 0.10 | 0.752 |
|  |  | 0.5 | 0.684 |
|  |  | 1 | 0.460 |
|  |  | 5 | 0.276 |
|  |  | 10 | 0.266 |
|  |  | 25 | 0.326 |
| 5:1 | 1.25 | 0 | 1.000 |
|  |  | 0.10 | 1.040 |
|  |  | 0.5 | 0.831 |
|  |  | 1 | 0.621 |
|  |  | 5 | 0.478 |
|  |  | 10 | 0.394 |
|  |  | 25 | 0.228 |

B. Polyallylamine/MC798 is effective in delivering siRNA to mammalian cells. CHO-luc cells, which contain an integrated luciferase gene, were maintained in medium supplemented with 0.5 mg/ml Geneticin (G418 Sulfate, Invitrogen).

Approximately 24 h prior to transfection, cells were plated at an appropriate density in 48-well plates and incubated overnight. Cultures were maintained in a humidified atmosphere containing 5% CO2 at 37° C. The indicated amount of GL3 siRNA was then combined with the indicated amount of polyallylamine (pA1) or pA1+MC798 in 25 μl Opti-MEM per well, incubated 5 min at RT and added to cells at 37° C. All polyallylamine containing solutions contained 2 mg/ml pA1 polymer. Ratios for pA1:MC798 are given as weight:weight. Cells were harvested after 24 h and assayed for luciferase activity using a Lumat LB 9507 (EG&G Berthold, Bad-Wildbad, Germany) luminometer. The amount of luciferase expression was recorded in relative light units. Numbers were then adjusted for control cells and are expressed as the percentage of firefly luciferase expression in the absence of siRNA or in cells treated with polycation and MC798 alone. Numbers are the average for three separate wells. Polyallylamine/MC798 was efficient in delivery of siRNA to mammalian cells in vitro and exhibited similar or less toxicity compared to ePEI (Table 8).

TABLE 8

Delivery of varying amount of GL3 siRNA to CHO-Luc cells using polyallylamine:MC798 amphipathic compound formulations.

| pVA/MC798 Ratio | μl per well | siRNA nM | Total Luciferase Activity | Relative Luciferase Activity |
|---|---|---|---|---|
| 2:1 | 0.500 | 0 | 6770490 | 1.000 |
|  |  | 10 | 5054467 | 0.747 |
|  | 0.625 | 0 | 9164157 | 1.000 |
|  |  | 10 | 3960493 | 0.432 |
|  | 0.750 | 0 | 6825740 | 1.000 |
|  |  | 10 | 3831537 | 0.561 |
| 3:1 | 0.500 | 0 | 8139340 | 1.000 |
|  |  | 10 | 5810067 | 0.714 |
|  | 0.625 | 0 | 7657740 | 1.000 |
|  |  | 10 | 4029553 | 0.526 |
|  | 0.750 | 0 | 5487000 | 1.000 |
|  |  | 10 | 1486010 | 0.271 |

Column Fractionation of Polycations

Column Prep: A 20×2.5 (length×Internal Diameter) Kontes Flex Column was packed with a preswelled and degassed slurry of sephacryl S-200 (Amersham). The column had a bed height of 97 mL and an exclusion volume of 25 mL, thus giving it an effective height of 72 mL.

Buffer: To 4 L of 2 mM Hepes/150 mM NaCl/10% MeOH, was added 1.0 mL acetic acid and 5 mL 2 M NaOH, to bring the final pH to 5.0.

Separation: To the top of the column was loaded, 3 mL ethoxylated PEI (Aldrich), poly(vinyl amine) (Polysceince), or poly(allylamine) (Aldrich) All the polymers were in $dH_2O$ at 100 mg/mL. Once the column was loaded it was connected to a low flow pump at run at 0.5 ml/minute and collected by time on a Foxy Jr. fraction collector. The locations of the polymers were determined using TNBS and the collected fractions containing the polymer were pooled into 8 fractions. These pooled fractions were then transferred to a 6,000-8,000 MWCO cellulose dialysis tubing (Fisher) and dialyzed for 48 h (2×20 L) against $dH_2O$ and freeze dried.

C. Polyvinylamine(pVA)/MC798/MC810 is effective in delivering siRNA to mammalian cells. siRNA Transfection reagentformulation—The pVA/MC798/MC810 siRNA transfection reagent formulation contains the cationic polymer, polyvinylamine (pVA), molecular weight 25,000 (Polysciences, Inc.), at 2 mg/ml and two cationic lipid components (MC798 and MC810) (Mirus) each at 0.5 mg/ml in 100% ethanol. This formulation was stored at 4° C.

siRNAs used during the course of these experiments—The firefly luciferase—specific siRNA used to knockdown luciferase target gene expression had the following sequences for each stand of the annealed, double stranded siRNA.

```
                                                 (SEQ ID 1)
5'-rCrUrUrArCrGrCrUrGrArGrUrArCrUrUrCrGrATT-3'

(SEQ ID 2)
5'-rUrCrGrArArGrUrArCrUrCrArGrCrGrUrArArTT-3'
```

Cell Lines and Maintenance—The Chinese hamster ovary cell (CHO-K1) (American Type Culture Collection, ATCC) line was maintained in F-12 HAM'S medium (Cellgro, Mediatech, Inc.) containing 10% fetal bovine serum (FBS) (Hyclone) and 0.1× penicillin/streptomycin (Invitrogen). The HepG2 cell line (ATCC) was maintained in Minimal Essential Medium Eagle (MEM) (Cellgro, Mediatech) containing 0.1 mM non-essential amino acids (Invitrogen), and 0.1× penicillin/streptomycin (Invitrogen). The CHO-Luc stable cell was created by transfection of plasmids pCIluc (Mirus) and pMir3 (encodes neomycin resistance gene, Mirus) into CHO-K1 cells. Two days post-transfection, the cells were trypsinized, diluted and replated in CHO-K1 growth media containing 0.5 mg/ml neomycin (GENETICIN® from Invitrogen) in order to select for stably transfected cells. After replating, the cells were grown in selective media until individual colonies formed. The colonies were isolated, expanded, and screened for high level luciferase expression. Multiple colonies gave rise to cell lines expressing high levels of luciferase expression, and one stable cell line, designated CHO-Luc clone 5, was used in the following experiments. The CHO-Luc cell line was maintained in CHO-K1 media with the addition of 0.5 mg/ml GENETICIN® to promote maintenance of the integrated plasmids. A Hepa1c1c7-Luc cell line stably expressing firefly luciferase was created in a similar manner to the CHO-Luc cell line except that the luciferase encoding plasmid was pMir68 which utilizes a ubiquitin promoter to drive expression of the luciferase gene. The stable cell line that was created has been designated Hepa-Luc. This cell line is maintained in Dulbecco's Modified Essential Media (Cellgro, Mediatech) containing 10% FBS, 0.1× penicillin/streptomycin and 0.5 mg/ml GENETICIN®. All cells were grown at 37° C. in 5% CO2 and 95% relative humidity.

Transfection of reporter plasmids into CHO-K1 and HepG2 cell lines—The following transfection protocol was used for both CHO-K1 and HepG2 cell lines. Cells were grown in T75 tissue culture flasks until approximately 50-70% confluence. Each flask of cells was then transfected simultaneously with two reporter plasmids: 15 μg of the firefly luciferase expression plasmid pMir116 (pGL-3) (Promega) and 50 ng of *Renilla* luciferase expression plasmid pMir122 (pRL-SV40) (Promega). The plasmids were transfected using 45 μl of TransIT-LT1 (Mirus) according to the manufacturer's instructions. Two hours post-transfection, the cells were trypsinized with 1 ml of trypsin, and resuspended in 12-14 ml of complete growth media. Aliquots (0.5 ml/well) of the cell suspensions were plated in 24 well plates (Greiner) and incubated an additional 2 hours. At this point the cells were ready for transfection with the anti-firefly luciferase siRNA.

Transfection of anti-firefly luciferase siRNA into mammalian cells using the pVA/lipid formulation—The following protocol was utilized for the transfection of the anti-firefly luciferase siRNA into both the CHO-K1 and HepG2 cells previously transfected with the firefly and *Renilla* luciferase plasmids, as well as the stable CHO-Luc and Hepa-Luc cell lines. In all cases, the transfections were performed on cells plated in 24 well plates at 50-70% confluence. For each transfection condition, 0.5-3.0 µl of the pVA/lipid reagent was added to 100 µl of Opti-MEM (Invitrogen) in a sterile plastic tube. The reagent was allowed to disperse for approximately 5 minutes, and then 15 µl of 1 µM anti-firefly luciferase siRNA was added to the tube, mixed gently by pipetting, and incubated for approximately 10 minutes at RT to allow for complex formation. Reagent alone controls were also set up in parallel using the same amounts of pVA/lipid reagent that were used to transfect the siRNA. Half of the media (250 µl) from each well of the 24 well plates was removed. The complexes (and reagent alone controls) were then added to duplicate wells of a 24 well plate (50 µl of complexes per well) making the total volume per well 300 µl and the final concentration of siRNA 25 nM per well. The plates were mixed gently by rocking to disperse the complexes and incubated at 37° C., 5% CO2 for approximately 24 hours (48 hours for Hepa-Luc transfections). During this time the siRNA was transfected into the cells and was utilized by the RNA interference pathway to inhibit firefly luciferase expression.

Measurement of luciferase gene expression in transiently transfected CHO-K1 and HepG2 cells and determination of target gene inhibition—After the transfected CHO-K1 and HepG2 cells were incubated for 24 hours, each well was washed with PBS. The PBS was removed, and the cells were lysed in 400 µl/well of Passive Lysis Buffer (PLB) (Promega) according to the manufacturer's instructions. Each cell lysate was assayed for both firefly luciferase and *Renilla* luciferase expression using the Dual-Luciferase Assay System (Promega) according to the manufacturer's instructions. 4 µl of each sample were assayed for firefly and *Renilla* luciferase activity and quantitated on a Berthold Technologies Centro LB 960 µlate luminometer. In order to quantitate the level of firefly luciferase knockdown, the firefly luciferase levels were first normalized to the *Renilla* luciferase levels to control for plasmid transfection efficiency. The normalized firefly luciferase levels were then compared to corresponding reagent alone transfected controls to determine the decrease in firefly luciferase expression due to the transfection of the anti-firefly luciferase siRNA.

Measurement of luciferase gene expression in siRNA-transfected CHO-Luc and Hepa-Luc stable cell lines and determination of target gene inhibition—After the transfected CHO-Luc and Hepa-Luc cells were incubated for 24 and 48 hrs hours, respectively, each well was washed with PBS. The PBS was removed, and the cells were lysed in 125 µl of LUX buffer (0.1 M KH2PO4, pH 7.8, 1 mM DTT, and 0.1% Triton X-100) by rocking for 15 minutes at room temperature. Each cell lysate was assayed for firefly luciferase and activity using a standard firefly luciferase assay system. 5 µl of each sample were assayed in a Berthold Technologies Centro LB 960 plate luminometer. In order to quantitate the level of firefly luciferase knockdown, the firefly luciferase levels in the siRNA-transfected cell lysates were compared to the corresponding reagent alone controls to determine the decrease in firefly luciferase expression due to the transfection of the anti-firefly luciferase siRNA.

Figure 13:
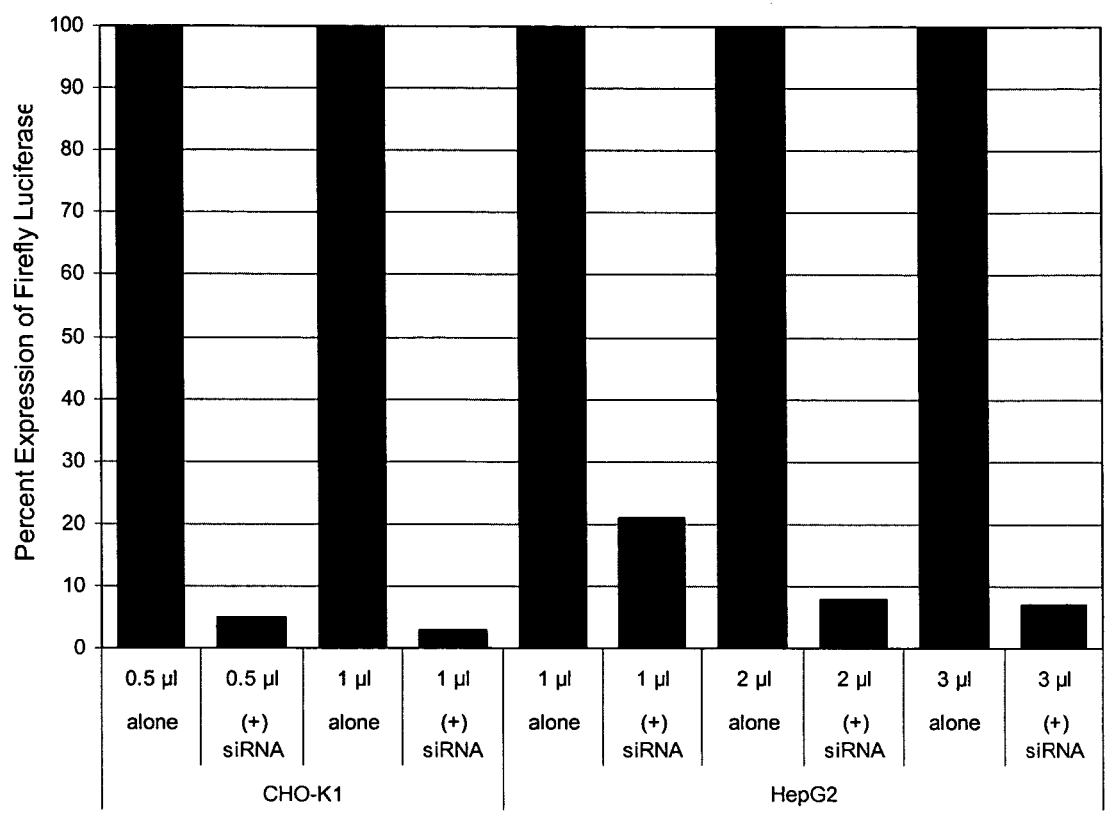
FIG. 13. Polyvinylamine/MC798/MC810 mediated delivery of siRNA results in strong inhibition of gene expression in transfected CHO-K1 cells and HegG2 mammalian cells.
Figure 14:
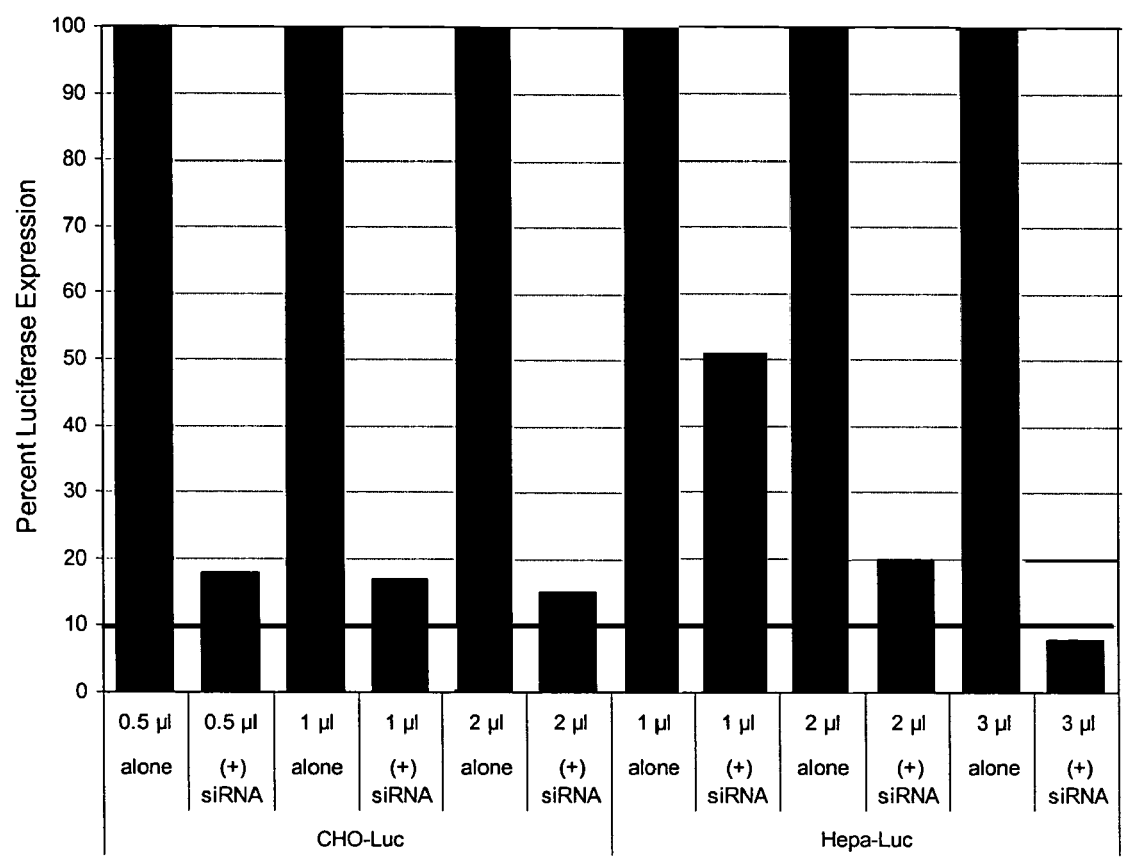
FIG. 14. Polyvinylamine/MC798/MC810 mediated delivery of siRNA results in strong inhibition of endogenous gene expression in CHO-Luc cells and Hepa-Luc mammalian cells FIG. 15. ePEI/MC798 siRNA delivery reagent can be effectively prepared in a dried form suitable for use in multi-well formats. Chart shows inhibition of luciferase expression following TransIT-TKO mediated delivery of siRNA to cells.

The pVA/lipid formulation was tested for its ability to deliver siRNA to mammalian cells and inhibit target gene expression through the RNA interference pathway. As illustrated in FIG. 13, the pVA/lipid formulation was highly effective at delivering functional siRNA that inhibited expression of the transiently transfected firefly luciferase target gene to CHO-K1 and HepG2 cells. Inhibition of target gene expression was reduced to as low as 3% of the reagent alone control in CHO-K1 cells and 7% of the reagent alone control in HepG2 cells, illustrating that the pVA/lipid formulation is a highly efficient siRNA transfection reagent. The pVA/lipid formulation was also tested for its ability to deliver siRNA to mammalian cells stably expressing the firefly luciferase target gene. In this case the luciferase gene is effectively an endogenous gene. The results obtained with these cells demonstrates the effectiveness of the pVA/lipid reagent in delivering siRNA to inhibit expression of an endogenous gene target. FIG. 14 illustrates the impressive inhibition of firefly luciferase expression that is seen upon delivery of the anti-firefly luciferase siRNA by the pVA/lipid formulation. In CHO-Luc cells, luciferase expression was decreased as low as 15% that of the reagent alone control. In Hepa-Luc cells, luciferase expression was decreased even further, 8% that of the reagent alone control when 3 µl of the pVA/lipid reagent was used.

4. Delivery of siRNA to Mammalian Cells Using 96-well TKO Plate Format

Sterile 96 well plates were obtained from tissue culture stocks (Grenier, Cell Star, No. 655180). Dilutions of TransIT-TKO were made in a sterile field using 100% ethanol. Stocks are prepared in such a way that 0.25 µl, 0.5 µl, 0.75 µl and 1 µl of the original 2.25 mg/ml TransIT-TKO reagent is added per well in 2 µl aliquots per well. TransIT-TKO reagent was dispensed (2 µl per well of each dilution) into plates in a sterile field using a Transferpette®-8, 2-20 µl multi-channel pipettor. Three rows of eight wells were dispensed for each dilution. Plates can also be made in which one dilution is used for the entire multiwell plate. Plates can also be made in which more than one dilution is used. Plates were wrapped in aluminum foil and transferred to a bell jar with vacuum. A vacuum of less than 1 Torr was maintained for ≧24 h. For some plates 2-5 µl siRNA-Luc+ (0.5-1.25 µM in 250 µl 100 mM NaCl/50 mM Tris-HCl, pH 8.0) was then added to each well and the drying process was repeated. Plates were stored dry until use.

CHO-luc and 3T3-lux cells, which contain an integrated luciferase gene, were maintained in medium supplemented with 0.5 mg/ml Geneticin (G418 Sulfate, Invitrogen). Approximately 24 h prior to transfection, cells were plated at an appropriate density in a T75 flask and incubated overnight. Other cells types were transfected with pGL-3-control (firefly luciferase, Promega, Madison Wis.) and pRL-SV40 (sea pansy luciferase, Promega, Madison, Wis.) using TransIT-LT1 transfection reagent as described above. All cultures were maintained in a humidified atmosphere containing 5% $CO_2$ at 37° C. Prior to the addition of cells to a 96-well plate containing dried TransIT-TKO transfection reagent, siRNA against firefly luciferase (siRNA-luc+) was added to 11 ml of OptiMEM to create a mixture with a working concentration of 50 nM. This solution was mixed by gentle vortexing. The siRNA/OptiMEM mixture was then added to the 96-well TKO plate (50 μl/well) and incubated at RT ≧30 min. Cells were washed with PBS, harvested with trypsin/EDTA, and suspended in media containing twice the normal amount of serum (i.e. F12 Hamms+20% FBS). The cells were counted using a hemacytometer and diluted in medium+20% FBS to 100,000-150,000 cells per ml. Cells (50 μl/well) were then added to the TKO plate (100 μl final volume/well, 25 nM siRNA). Plates were rocked gently and incubated at 5% $CO_2$ at 37° C. for 24 h.

Figure 15:
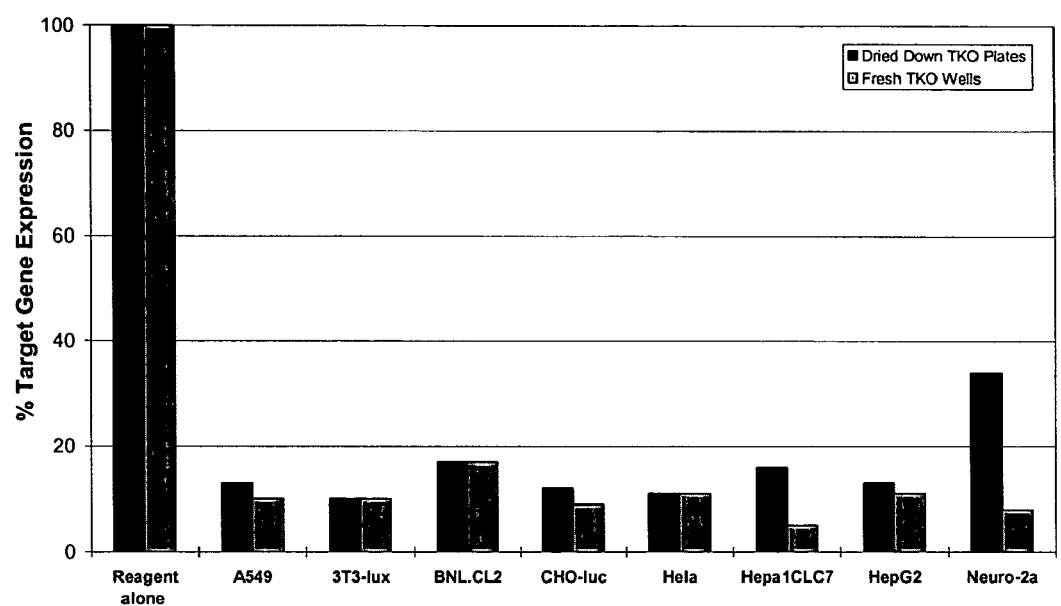

Cells were harvested after 24 h and assayed for luciferase activity using a Lumat LB 9507 (EG&G Berthold, Bad-Wildbad, Germany) luminometer. The amount of luciferase expression was recorded in relative light units. Numbers were then adjusted for control cells and are expressed as the percentage of firefly luciferase expression in the absence of siRNA. Numbers are the average for at least four separate wells of cells (FIG. 15, black bars). Delivery is compared with liquid protocol (examples 2A-G, gray bars). Similar results were observed when plates were formulated containing siRNA prior to drying.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A composition for delivery of siRNA to a mammalian cell comprising: said siRNA, a first amphipathic compound that is a cationic lipid, a second amphipathic compound that is a cationic lipid and a polycation, wherein the polycation is not a DNA-binding protein and is selected from the group consisting of: polyvinylamine, polyallylamine, polyethylenimine and ethoxylated polyethylenimine wherein said second amphipathic compound consists of an amphipathic compound having the structure:

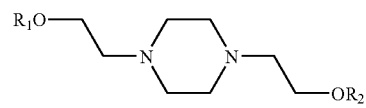

wherein R1 and R2 are selected from the group consisting of a C6 to C24 alkane, C6-C24 alkene, mono-substituted alkyl silane, di-substituted alkyl silane, tri-substituted alkyl silane, cycloalkyl, sterol, steroid, substituted lipid, acyl segment of a fatty acid, hydrophobic hormone, and hydrophobic hormone analog.

2. The composition of claim 1 wherein said second amphipathic compound consists of an amphipathic compound having the structure:

---

SEQUENCE LISTING

<160> NUMBER OF SEQ ID NOS: 3

<210> SEQ ID NO 1
<211> LENGTH: 20
<212> TYPE: DNA
<213> ORGANISM: Photinus pyralis

<400> SEQUENCE: 1
cuuacgcuga guacuucgat                                              20

<210> SEQ ID NO 2
<211> LENGTH: 21
<212> TYPE: DNA
<213> ORGANISM: Photinus pyralis

<400> SEQUENCE: 2
ucgaaguacu cagcguaagt t                                            21

<210> SEQ ID NO 3
<211> LENGTH: 25
<212> TYPE: RNA
<213> ORGANISM: Photinus pyralis

<400> SEQUENCE: 3
ccucuucaau caguuacaau uuaua                                        25

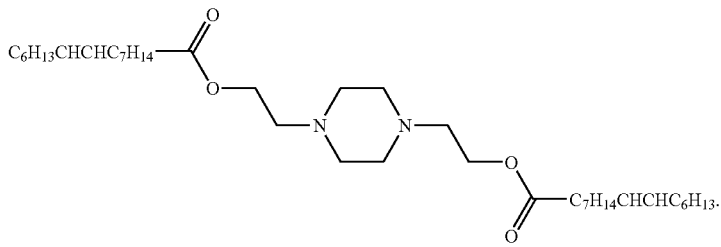

3. A composition for delivery of siRNA to a mammalian cell comprising: said siRNA, a first amphipathic compound that is a cationic lipid, a second amphipathic compound that is a cationic lipid and a polycation, wherein the polycation is not a DNA-binding protein and is selected from the group consisting of: polyvinylamine, polyallylamine, polyethylenimine and ethoxylated polyethylenimine wherein said first amphipathic compound consists of an amphipathic compound having the structure:

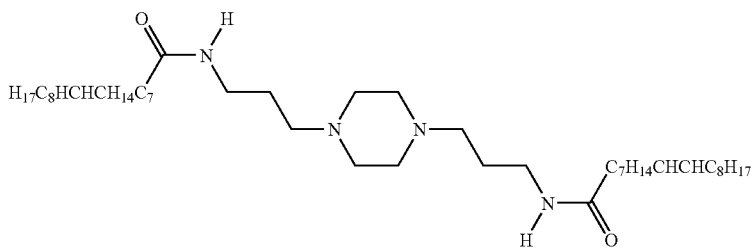

and said second amphipathic compound consists of an amphipathic compound having the structure:

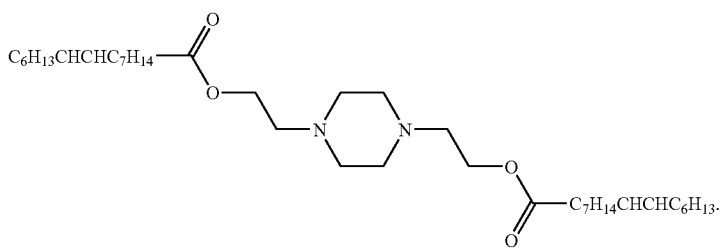

4. A kit for siRNA transfection comprising: a container containing a preparation comprising: a first amphipathic compound that is a cationic lipid, a second amphipathic compound that is a cationic lipid and a polycation wherein the polycation is not a DNA-binding protein and is selected from the group consisting of: polyvinylamine, polyallylamine, polyethylenimine and ethoxylated polyethylenimine, and instructions for an amount of the preparation and an amount of the siRNA to be admixed wherein said second amphipathic compound consists of an amphipathic compound having the structure:

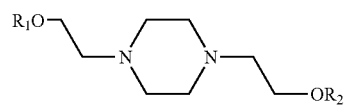

wherein R1 and R2 are selected from the group consisting of a C6 to C24 alkane, C6-C24 alkene, mono-substituted alkyl silane, di-substituted alkyl silane, tri-substitued alkyl silane, cycloalkyl, sterol, steroid, substituted lipid, acyl segment of a fatty acid, hydrophobic hormone, and hydrophobic hormone analog.

5. The kit of claim 4 wherein said second amphipathic compound consists of an amphipathic compound having the structure:

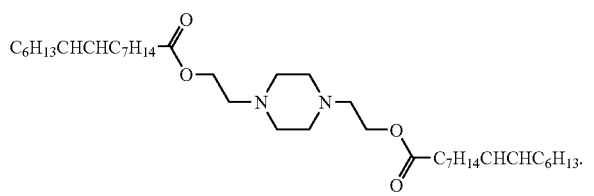

6. A kit for siRNA transfection comprising: a container containing a preparation comprising: a first amphipathic compound that is a cationic lipid, a second amphipathic compound that is a cationic lipid and a polycation wherein the polycation is not a DNA-binding protein and is selected from the group consisting of: polyvinylamine, polyallylamine, polyethylenimine and ethoxylated polyethylenimine, and instructions for an amount of the preparation and an amount of the siRNA to be admixed wherein said first amphipathic compound consists of an amphipathic compound having the structure:

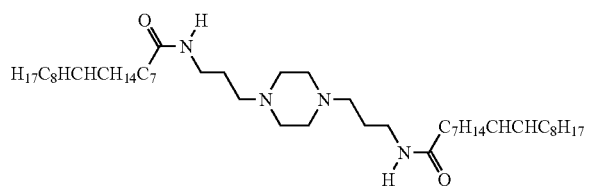

and said second amphipathic compound consists of an amphipathic compound having the structure:

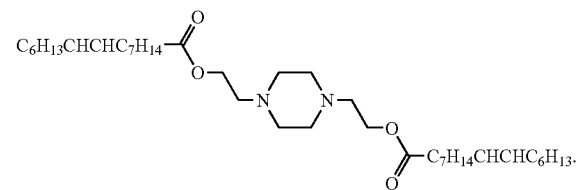

* * * * *